US010844088B2

(12) United States Patent
Platteeuw et al.

(10) Patent No.: US 10,844,088 B2
(45) Date of Patent: Nov. 24, 2020

(54) PROCESS FOR THE PREPARATION OF ESTETROL

(71) Applicant: Donesta Bioscience B.V., Zeist (NL)

(72) Inventors: Johannes Jan Platteeuw, Boxtel (NL); Herman Jan Tijmen Coelingh Bennink, Zeist (NL); Franciscus Wilhelmus Petrus Damen, Wijchen (NL); Michiel Christian Alexander Van Vliet, Delft (NL)

(73) Assignee: ESTETRA SPRL, Liege (BE)

(*) Notice: Subject to any disclaimer, the term of this patent is extended or adjusted under 35 U.S.C. 154(b) by 381 days.

(21) Appl. No.: 15/426,209

(22) Filed: Feb. 7, 2017

(65) Prior Publication Data

US 2017/0369521 A1 Dec. 28, 2017

Related U.S. Application Data

(63) Continuation of application No. 14/233,362, filed as application No. PCT/NL2012/050514 on Jul. 18, 2012, now abandoned.

(60) Provisional application No. 61/509,168, filed on Jul. 19, 2011.

(30) Foreign Application Priority Data

Jul. 19, 2011 (EP) .................................. 11174509

(51) Int. Cl.
*C07J 1/00* (2006.01)
*C07J 13/00* (2006.01)
*C07J 75/00* (2006.01)

(52) U.S. Cl.
CPC ............. *C07J 1/007* (2013.01); *C07J 1/0059* (2013.01); *C07J 13/005* (2013.01); *C07J 75/00* (2013.01); *Y02P 20/55* (2015.11)

(58) Field of Classification Search
CPC ......... C07J 1/007; C07J 1/0059; C07J 13/005
See application file for complete search history.

(56) References Cited

U.S. PATENT DOCUMENTS

| | | | |
|---|---|---|---|
| 3,138,588 A | 6/1964 | Smith | |
| 3,177,206 A | 4/1965 | Smith et al. | |
| 3,433,785 A | 3/1969 | Phillips et al. | |
| 4,739,078 A | 4/1988 | Pearlman | |
| 4,792,620 A * | 12/1988 | Paulik | B01J 31/0231 560/232 |
| 4,923,640 A | 5/1990 | Bohlmann et al. | |
| 5,340,586 A | 8/1994 | Pike et al. | |
| 6,117,446 A | 9/2000 | Place | |
| 6,541,465 B2 | 4/2003 | Loozen et al. | |
| 6,723,348 B2 | 4/2004 | Faham et al. | |
| 7,723,320 B2 | 5/2010 | Bunschoten et al. | |
| 7,732,430 B2 | 6/2010 | Bunschoten et al. | |
| 7,871,995 B2 | 1/2011 | Bunschoten et al. | |
| 7,923,440 B2 | 4/2011 | Bunschoten et al. | |
| 7,943,604 B2 | 5/2011 | Coelingh Bennink et al. | |
| 8,026,228 B2 | 9/2011 | Coelingh Bennink et al. | |
| 8,048,869 B2 | 11/2011 | Bunschoten et al. | |
| 8,236,785 B2 | 8/2012 | Coelingh Bennink | |
| 8,367,647 B2 | 2/2013 | Coelingh Bennink et al. | |
| 8,518,923 B2 | 8/2013 | Visser et al. | |
| 8,987,240 B2 | 3/2015 | Coelingh Bennink et al. | |
| 8,987,484 B2 | 3/2015 | Pascal | |
| 9,034,854 B2 | 5/2015 | Coelingh Bennink et al. | |
| 9,040,509 B2 | 5/2015 | Coelingh Bennink et al. | |
| 9,238,035 B2 | 1/2016 | Foidart et al. | |
| 9,561,238 B2 | 2/2017 | Coelingh Bennink et al. | |
| 9,579,329 B2 | 2/2017 | Wouters et al. | |
| 9,603,860 B2 | 3/2017 | Perrin et al. | |
| 9,884,064 B2 | 2/2018 | Platteeuw et al. | |
| 9,987,287 B2 | 6/2018 | Platteeuw et al. | |
| 9,988,417 B2 | 6/2018 | Ferreiro Gil et al. | |
| 10,179,140 B2 | 1/2019 | Perrin et al. | |
| 2002/0132801 A1 | 9/2002 | Heil et al. | |
| 2004/0009960 A1 | 1/2004 | Heil et al. | |
| 2004/0192620 A1 | 9/2004 | Bunschoten et al. | |
| 2004/0198671 A1 | 10/2004 | Bunschoten et al. | |
| 2005/0032755 A1 | 2/2005 | Van Look et al. | |

(Continued)

FOREIGN PATENT DOCUMENTS

| | | |
|---|---|---|
| CL | 200501207 | 5/2005 |
| CL | 201400802 | 4/2014 |

(Continued)

OTHER PUBLICATIONS

Nicolaou et al, Angewandte Chemie International Edition, Oxidation of Silyl Enol Ethers by Using IBX and IBX N-oxide Complexes: A Mild and Selectiove Reaction for the Synthesis of Enones, 2002, 41(6), pp. 996-1000. (Year: 2002).*

Zaragoza Dorwald , Side Reactions in Organic Synthesis, 2005, Wiley-VCH Verlag GmbH & Co. KGaA, Weinheim, Preface. p. IX. (Year: 2005).*

Li et al, Steroids, Stereoselective Synthesis of Some Methyl-substituted Steroid Hormones and Their In Vitro Cytotoxic Activity Against Human Gastric Cancer Cell Line MGC-803, 2010, 75, pp. 859-869. (Year: 2010).*

Norskov et al, Nature Chemistry, Towards the Computational Design of Solid Catalysts, 2009, 1, pp. 37-46 (Year: 2009).*

Bull, et al. "Synthesis and structure-activity studies of 8a- and 9beta-analogues of 14,17-ethanoestradiol", J. Chem. Soc., Perkin Trans. 1, 2000, pp. 1003-1013.

(Continued)

*Primary Examiner* — Paul A Zucker
(74) *Attorney, Agent, or Firm* — Foley & Lardner LLP; Sunit Talapatra

(57) ABSTRACT

The present invention relates to a process for the preparation of estra-1,3,5(10)-trien-3, 15a, 16a, 17β-tetraol (estetr-01), via a silyl enol ether derivative 17-B-oxy-3-A-oxy-estra-1, 3,5(10), 16-tetraene, wherein A is a protecting group and B is —Si(R²)₃. The invention further relates to a process for the synthesis of 3-A-oxy-estra-1,3,5(10), 15-tetraen-17-one, in which A is a protecting group, via silyl enol ether derivative 17-B-oxy-3-A-oxy-estra-1,3,5(10),16-tetraene, and B is —Si(R²)₃.

12 Claims, 10 Drawing Sheets

(56) References Cited

U.S. PATENT DOCUMENTS

| | | |
|---|---|---|
| 2005/0070488 A1 | 3/2005 | Coelingh Bennik et al. |
| 2005/0147670 A1 | 7/2005 | Hsu et al. |
| 2006/0063723 A1 | 3/2006 | Coelingh Bennink et al. |
| 2006/0211669 A1 | 9/2006 | Verhaar et al. |
| 2007/0048369 A1 | 3/2007 | Foreman et al. |
| 2007/0286819 A1 | 12/2007 | Devries et al. |
| 2008/0113953 A1 | 5/2008 | De Vries et al. |
| 2010/0093679 A1 | 4/2010 | Heil et al. |
| 2011/0250274 A1 | 10/2011 | Shaked et al. |
| 2012/0220556 A1 | 8/2012 | Heil et al. |
| 2014/0010791 A1 | 1/2014 | Wandless et al. |
| 2014/0107358 A1 | 4/2014 | Pascal |
| 2014/0235882 A1 | 8/2014 | Platteeuw et al. |
| 2015/0045300 A1 | 2/2015 | Ahuja et al. |
| 2015/0105362 A1 | 4/2015 | Verhaar et al. |
| 2015/0133413 A1 | 5/2015 | Bennink et al. |
| 2015/0182540 A1 | 7/2015 | Heil et al. |
| 2016/0310506 A1 | 10/2016 | Platteeuw et al. |
| 2016/0367567 A1 | 12/2016 | Jaspart et al. |
| 2017/0019886 A1 | 1/2017 | Patel et al. |
| 2017/0216318 A1 | 8/2017 | Perrin et al. |
| 2017/0369521 A1 | 12/2017 | Platteeuw et al. |
| 2018/0153801 A1 | 6/2018 | Jaspart et al. |
| 2018/0169022 A1 | 6/2018 | Jaspart et al. |
| 2018/0185271 A1 | 7/2018 | Jaspart et al. |
| 2018/0265540 A1 | 9/2018 | Verhaar et al. |

FOREIGN PATENT DOCUMENTS

| | | |
|---|---|---|
| CN | 1197387 A | 10/1998 |
| CN | 101443015 A | 5/2009 |
| CN | 101541326 A | 9/2009 |
| CN | 101631536 A | 1/2010 |
| CN | 102058604 A | 5/2018 |
| DE | 21 29 943 A | 12/1971 |
| DE | 144266 A | 10/1980 |
| EP | 0 277 676 A1 | 8/1988 |
| EP | 0 371 466 A1 | 6/1990 |
| EP | 0 646 592 A | 4/1995 |
| EP | 2 001 0201.7 | 11/2002 |
| EP | 2 077 272 A8 | 7/2009 |
| EP | 2 077 273 A9 | 7/2009 |
| EP | 2 077 322 | 7/2009 |
| EP | 2 077 812 | 7/2009 |
| EP | 2 085 373 A1 | 8/2009 |
| EP | 2 383 279 A1 | 11/2011 |
| EP | 2 714 710 B1 | 4/2014 |
| EP | 3 046 928 B1 | 7/2016 |
| EP | 3 106 148 A1 | 12/2016 |
| JP | S63-258487 A | 10/1988 |
| JP | 2005-523283 T | 8/2005 |
| JP | 2010-513514 T | 4/2010 |
| WO | WO-95/17895 | 7/1995 |
| WO | WO-00/42955 A1 | 7/2000 |
| WO | WO-01/05806 | 1/2001 |
| WO | WO-01/40255 | 6/2001 |
| WO | WO-02/49675 | 6/2002 |
| WO | WO-02/094275 A1 | 11/2002 |
| WO | WO-02/094276 A1 | 11/2002 |
| WO | WO-02/094278 A1 | 11/2002 |
| WO | WO-02/094279 A1 | 11/2002 |
| WO | WO-03/018026 A1 | 3/2003 |
| WO | WO-03/041718 A1 | 5/2003 |
| WO | WO-2004/006936 A1 | 1/2004 |
| WO | WO-2004/019954 | 3/2004 |
| WO | WO-2004/041289 | 5/2004 |
| WO | WO 2004/041839 A2 * | 5/2004 |
| WO | WO-2004/041839 A2 | 5/2004 |
| WO | WO-2004/103377 A1 | 12/2004 |
| WO | WO-2005/030175 | 4/2005 |
| WO | WO-2005/030176 | 4/2005 |
| WO | WO-2005/051400 | 6/2005 |
| WO | WO-2005/105103 | 11/2005 |
| WO | WO-2005/115349 | 12/2005 |
| WO | WO-2005/115351 | 12/2005 |
| WO | WO-2006/027347 | 3/2006 |
| WO | WO-2006/120035 | 11/2006 |
| WO | WO-2006/125800 A2 | 11/2006 |
| WO | WO-2007/081206 | 7/2007 |
| WO | WO-2007/106264 | 9/2007 |
| WO | WO-2008/003363 | 1/2008 |
| WO | WO-2008/003432 | 1/2008 |
| WO | WO-2008/156365 | 12/2008 |
| WO | WO-2010/033832 A2 | 3/2010 |
| WO | WO-2010/089078 A1 | 8/2010 |
| WO | WO-2010/149273 | 12/2010 |
| WO | WO-2011/128336 | 10/2011 |
| WO | WO-2012/000981 | 1/2012 |
| WO | WO-2012/055840 A1 | 5/2012 |
| WO | WO-2012/164095 | 12/2012 |
| WO | WO-2012/164096 | 12/2012 |
| WO | WO-2013/012326 A1 | 1/2013 |
| WO | WO-2013/021025 A1 | 2/2013 |
| WO | WO-2013/090117 | 6/2013 |
| WO | WO-2014/159377 A1 | 10/2014 |
| WO | WO-2014/189836 | 11/2014 |
| WO | WO-2015/040051 | 3/2015 |
| WO | WO-2015/086643 A1 | 6/2015 |
| WO | WO-2016/053946 | 4/2016 |
| WO | WO-2016/187269 | 11/2016 |
| WO | WO-2016/203006 A1 | 12/2016 |
| WO | WO-2016/203009 | 12/2016 |
| WO | WO-2016/203011 | 12/2016 |
| WO | WO-2016/203044 A1 | 12/2016 |
| WO | WO-2016/207298 | 12/2016 |
| WO | WO-2018/024912 | 2/2018 |
| WO | WO-2018/065076 | 4/2018 |

OTHER PUBLICATIONS

Cantrall, et al. "The Synthesis of C-15 Beta-Substituted Estra-1,3,5(10)-trienes. I", J. Org. Chem., Jan. 1964, vol. 29, pp. 64-68.

Cantrall, et al. "The Synthesis of C-15 Beta-Substituted Estra-1,3,5(10)-trienes. II", J. Org. Chem., Jan. 1964, vol. 29, pp. 214-217.

Dorwald, "Side Reactions in Organic Synthesis—A Guide to Successful Synthesis Design", Wiley-VCH Verlag GmbH & Co. KGaA, Weinheim, Preface, p. IX.

Fishman, et al. "Synthesis of Epimeric 15-Hydroxyestriols, New and Potential Metabolites of Estradiol", The Journal of Organic Chemistry, Aug. 1968, vol. 33, No. 8, pp. 3133-3135.

International Search Report of PCT/NL2012/050514 dated Oct. 10, 2012.

Johnson, et al. "14-Isoestrone Methyl Ether and its Identity with Totally Synthetic Material", J. Am. Chem. Soc., Apr. 20, 1957, vol. 79, pp. 2005-2009.

Larock, et al. "A Simple, Effective, New, Palladium-Catalyzed Conversion of Enol Silanes to Enones and Enals", Tetrahedron Letters (1995) vol. 36, No. 14, pp. 2423-2426.

Li et al. "Stereoselective synthesis of some methyl-substituted steroid hormones and their in vitro cytotoxic activity against human gastric cancer cell line MGC-803", Steroids, vol. 75, 2010, pp. 859-869.

Nambara, et al. "Synthesis of Esterol Monoglucuronides", Steroids, 1976, vol. 27, pp. 111-121.

Nicolaou, et al., "Oxidation of Silyl Enol Ethers by Using IBX and IBX N-Oxide Complexes: A Mild and Selective Reaction for the Synthesis of Enones", Angew. Chem., 2002, vol. 114, No. 6, pp. 1038-1042.

Ozanne, et al. "A Stabilized Formulation of IBX (SIBX) for Safe Oxidation Reactions Including a New Oxidative Demethylation of Phenolic Methyl Aryl Ethers", Organic Letters (2003) vol. 5, No. 16, pp. 2903-2906.

Poirier, et al. "Synthesis of 17beta-Estradiol Derivatives With N-Butyl, N_Methyl Alkylamide Side Chain at Position 15", Tetrahedron, 1991, vol. 47, No. 37, pp. 7751-7766.

Smith, III. et al. "A New Modular Indole Synthesis. Construction of the Highly Strained CDEF Parent Tetracycle of Nodulisporic Acids A and B", Organic Letters, 2006, vol. 8, No. 10, pp. 2167-2170.

(56) References Cited

OTHER PUBLICATIONS

Smith, III. et al. "Indole Diterpene Synthetic Studies: Development of a Second-Generation Synthetic Strategy for ( )-Nodulisporic Acids A and B", J. Org. Chem., 2007, vol. 72, pp. 4611-4620.
Suzuki, et al. "Synthesis of 15a-hydroxyestrogen 15-N-acetylglucosaminides", Steroids, 1995, vol. 60, pp. 277-284.
Yamada, et al. "Pre-MIBSK for industrial-scale alcohol oxidation", Specialty Chemicals Magazine, Catalysts, Jan. 2011, pp. 18-20.
"Pharmaceutics," Editor in Chief: Liu Shubao, p. 153, Henan Science and Technology Press (published on Jul. 31, 2007).
Al-Jefout et al., "Continuous Norethisterone Acetate versus Cyclical Drospirenone 3 mg/Ethinyl Estradiol 20 ug for the Management of Primary Dysmenorrhea in Young Adult Women," Journal of Pediatric and Adolescent Gynecology, vol. 29, No. 2, pp. 143-147, XP029421056 (Sep. 2015).
Andersch and Milsom: "An epidemiologic study of young women with dysmenorrhea", Am J Obstet Gynecol, 144(6), p. 655-660 (1982).
Anderson and Spencer: "Risk factors for venous thromboembolism", Circulation, 107, I-9-I-16.
Anderson et al., Effects of conjugated equine estrogen in postmenopausal women with hysterectomy: the Women's Health Initiative randomized controlled trial, JAMA (2004), vol. 291(14), pp. 1701-1712.
Apter et al., "Bleeding pattern and cycle control with estetrol-containing combined oral contraceptives: results from a phase II, randomized, dose-finding study (FIESTA)," Contraception 94 (2016) pp. 366-373.
Archer et al., "A randomized, double-blind, placebo-controlled study of tne lowest effective dose of drospirenone with 17β-estradiol for moderate to severe vasomotor symptoms in postmenopausal women," (2014) Menopause, vol. 21(3), pp. 227-235.
Arnal et al., "Tissue specificity of the membrane vs nuclear actions of estrogen receptor alpha: insights from targeted mutations in mouse models," Archives of Cardiovascular Diseases Supplements, (Apr. 2016) vol. 8, 99-217, Abstract 0333.
Bagot et al: "The effect of estrone on thrombin generation may explain the different thrombotic risk between oral and transdermal hormone replacement therapy", J Thromb Haemost., 8(8):1736-1744 (2010).
Bennink et al., "Estetrol review: profile and potential clinical applications," Climacteric (2008) vol. 11, Suppl. 1, pp. 7-58.
Bennink et al., "Estetrol review: profile and potential clinical applications," Climacteric, vol. 11, No. Suppl. 1, (2008) pp. 47-58.
Bennink et al., "Pharmacodynamic effects of the fetal estrogen estetrol in postmenopausal women: results from a multiple-rising-dose study," (2017) Menopause 24(6), pp. 677-685.
Bennink et al., "Pharmacokinetics of the fetal estrogen estetrol in a multiple-rising-dose study in postmenopausal women," (2017) Climacteric.20(3), pp. 285-289.
Bianchi, "Estetrol: Desde un estrogeno fetal hasta el tratamiento de la menopausia", (1905) Rev Chil Obstet Ginecol, 74(2): 123-126.
Bjarnason et al., "Acute and long-term estradiol kinetics in smoking postmenopausal women," (2012) Climacteric, vol. 15(5), pp. 449-454.
Bosworth et al., "Depressive symptoms, menopausal status, and climacteric symptoms in women at midlife," (2001) Psychosom Med., 63(4):603-8.
Cainelli, et al. "Catalytic Hydroxylation of Olefins by Polymer-Bound Osmium Tetroxide", J. Chem. Soc., Chem, Commun. (1989), pp. 45-47.
Callejo et al: "Effect of a low-dose oral contraceptive containing 20 microg ethinylestradiol and 150 microg desogestrel on dysmenorrhea", Contraception, 68(3), p. 183-188 (2003).
Chemical Land data sheet: LiAlH4 (lithium aluminum hydride). Accessed May 23, 2010.
Clive, et al. "Use of Radical Ring-Opening for Introduction of Alkyl and Substituted Alkyl Groups with Stereochemical Control: A Synthetic Application of Cyclopropylcarbinyl Radicals" J. Org. Chem. (1991) vol. 56, pp. 3801-3814.

Coelingh Bennink et al. 9th European Congress of Endocrinology Meeting Abstract No. S16,2, Endocrine Abstracts, vol. 14 (2007).
Coelingh Bennink et al., Ovulation inhibition by estetrol in an in vivo model, (2008) Contraception, vol. 77(3), pp. 186-190, XP02247767.
Coelingh Bennink Herjan J T et al, "Clinical effects of the fetal estrogen estetrol in a multiple-rising-dose study in postmenopausal women," (2016) Maturitas, Elsevier, Amsterdam, NL vol. 91, pp. 93-100, XP029649879.
Dahlback et al: "Familial thrombophilia due to a previously unrecognized mechanism characterized by poor anticoagulant response to activated protein C: prediction of a cofactor to activated protein C", Proc Natl Acad Sci U S A., 90(3), p. 1004-1008 (1993).
Davis et al: "Oral contraceptives for dysmenorrhea in adolescent girls: a randomized trial", Obstet Gynaecol, 106(1): 97-104 (2005).
De Bastos et al: "Combined oral contraceptives: venous thrombosis", Cochrane Database Syst Rev, (3):CD010813 (2014).
Dinger et al., Effectiveness of Oral Contraceptive Pills in a Large U.S. Cohort Comparing Progestogen and Regimen, Obstet. & Gynecol., 117(1):33-40 (2011).
Dinger et al., Oral Contraceptive Effectiveness According to Body Mass Index, Weight, Age, and Other Factors, Am. J. Obstet. Gynecol., 201:263e1-9 (2009).
Dinger et al: "Risk of venous thromboembolism and the use of dienogest- and drospirenone-containing oral contraceptives: results from a German case-control study", J Fam Plann Reprod Health Care, 36(3):123-129.
Dionne, et al. "D-ring allyl derivatives of 17beta-and 17alpha-estradiols: Chemical synthesis and 13C NMR data" Steroids (1997) vol. 62, pp. 674-681, Abstract only.
Duijkers et al., "Inhibition of ovulation by administration of estetrol in combination with drospirenone or levonorgestrel: Results of a phase II dose-finding pilot study," The European Journal of Contraception and Reproductive Health Care (2015) vol. 20, pp. 476-489.
Duijkers et al., A randomized study comparing the effect on Ovarian activity of a progestogen-only pill (POP) containing desogestrel and a new POP containing drospirenone in a 24/4 regimen, Euro. J. Contracept. & Repro. Health Care, 20(6):419-27 (2015).
Elger et al., Conception and pharmacodynamics profile of drospirenone, Steriods, 68(10):891-905 (2003).
Endrikat et al: "A twelve-month comparative clinical investigation of two low-dose oral contraceptives containing 20 micrograms ethinylestradiol/75 micrograms gestodene and 20 micrograms ethinylestradiol/150 micrograms desogestrel, with respect to efficacy, cycle control and tolerance", Contraception, 52(4), p. 229-235 (1995).
Erkkola "Role of progestins in contraception", Acta Obstet Gynecol Scand., 84(3), pp. 207-216 (2005).
Foidart, "Estelle?, Estetrol and drospirenone in oral contraception: E4 FREEDOM TM Phase 3 clinical study design," Presented at Eur. Soc. Contraception & Reprod. Health, 14th Cong, 2nd Global Conf. (May 5, 2016).
Foidart, "Estetrol, the first human, physiological Selective Estrogen Receptor Modulator," Presented at Eur. Soc. Contraception & Reprod. Health, 14th Cong, 2nd Global Conf. (May 5, 2016).
French: "Dysmenorrhea", Am Fam Physician, 71(2): 285-291 (2005).
Gardouh et al: "Preparation and characterization of mucoadhesive buccal film for delivery of meloxicam", (2013) British J. of Pharmaceutical Research, 3(4): 743-766.
Green et al. J. Chem. Soc., pp. 2532-2543 (1961).
Greene, Theodora W. et al. Protective Groups in Organic Synthesis, 3rd edition, pp. 113-179.
Haque et al: "Development of polymer-bound fast-dissolving metformin buccal film with disintegrants", (2015) Int. J. of Nanomedicine, 10: 199-205.
Harel et al., "Dysmenorrhea in adolescents and young adults: an update on pharmacological treatments and management strategies," Expert Opinion on Pharmacotherapy, vol. 3 No. 15, (Sep. 2012) pp. 2157-2170, XP055389783.
Harlow et al., "Executive summary of the Stages of Reproductive Aging Workshop 10: addressing the unfinished agenda of staging reproductive aging," (2012) Menopause, vol. 19(4).

(56) References Cited

OTHER PUBLICATIONS

Harrington et al: "Cross-sectional association of endogenous steroid hormone, sex hormone-binding globulin, and precursor steroid levels with hemostatic factor levels in postmenopausal women", J Thromb Haemost., 15(1), p. 80-90 (2017).
Heathcock et al.J. Am. Chem. Soc., vol. 104, pp. 6081-6091 (1982).
Heinemann et al., "The Menopause Rating Scale(MRS) as outcome measure for hormone treatment? A validation study," (2004) Health Qual Life Outcomes, pp. 2:67.
Heinemann et al., International versions of the Menopause Rating Scale (MRS), 2003, Health Qual Life Outcomes, pp. 1:28.
Heinemann et al., The Menopause Rating Scale (MRS) scale: A methodological review, 2004, Health Qual Life Outcomes, pp. 2:45.
Hendrix and Alexander: "Primary dysmenorrhea treatment with a desogestrel-containing low-dose oral contraceptive", 66(6), p. 393-399 (2002).
Hilditch et al., "A menopause specific quality of life questionnaire: development and psychometric properties," (1996) Maturitas, vol. 24(3), pp. 161-175.
Ichiro Minami et al. Tetrahedron, vol. 42, pp. 2971-2977 (1986).
Jick et al: "Risk of idiopathic cardiovascular death and nonfatal venous thromboembolism in women using oral contraceptives with differing progestagen components", Lancet, 346(8990): p. 1589-1593.
Kelly, et al. "Synthetic Steroids. Part III. The Preparation of 3beta,15beta,17beta-Trihydroxy-androst-5-ene and the Attempted Preparation of 3beta,15alpha,17beta-Trihydroxy-androst-5-ene", J. Chem. Soc. (1968), pp. 416-421.
Kluft Cornelis et al: "Reduced hemostatic effects with drospirenone-based oral contraceptives containing estetrol vs ethinyl estradiol", Contraception, vol. 95, n?2, p. 140-147.
Kluft, "Effects on estrogenic and haemostatic variables of estetrol in combination with dtospirenone," Presented at Eur. Soc. Contraception & Reprod. Health, 14th Cong, 2nd Global Conf. (May 5, 2016).
Lidegaard et al: "Hormonal contraception and risk of venous trhomboembolism: national follow-study", BMJ, 339:b2890.
Lidegaard et al: "Risk of venous thromboembolism from use of oral contraceptives containing different progestogens and oestrogen doses: Danish cohort study, 2001-9", BMJ, 343:d6423.
Lianmei et al., "Major research advances in estetrol," (2009) J Reprod Med, vol. 18(3), pp. 305-308.
Magnus, et al. "Applications of the Beta-Azidonation Reaction to Organic Synthesis. alpha Beta-Enones, Conjugate Addition, and y-Lactam Annulation", J. Am. Chem. Soc. (1998), vol. 120, pp. 12486-12499.
Matsui, et al. "Synthesis of Isomeric 5alpha-Androstane-3, 15, 17beta-triols", J. Chem. Soc., Perkin Trans. I, (1976), pp. 1429-1432.
Mawet et al., "Unique effects on hepatic function, lipid metabolism, bone and growth endocrine parameters of estetrol in combined oral contraceptives," The European Journal of Contraception and Reproductive Health Care, (2015) vol. 20, pp. 463-475.
Meulenbroeks et al., "21 7 versus 24 4 day monophasic regimens of combined oral contraceptives for contraception." Cochrane Database of Systematic Reviews 2015, Issue 7. Art. No. CD011781.
Mueller et al. The Journal of Organic Chemistry, 26 (7), pp. 2403-2413 (1961).
Notelovitz et al., "Initial 17β-Estradiol Dose for Treating Vasomotor Symptoms," (2000) Obstetrics and Gynaecology, vol. 95(5), pp. 726-731.
Odlind et al: "Can changes in sex hormone binding globulin predict the risk of venous thromboembolism with combined oral contraceptive pills?", Acta Obstet. Gynecol. Scand., 81(6), p. 482-490.
Fine (Advances in Therapy, vol. 28, No. 2, pp. 87-90).
Poort et al: "A common genetic variation in the 3'-untranslated region of the prothrombin gene is associated with elevated plasma prothrombin levels and an increase in venous thrombosis", Blood, 88(10), p. 3698-3703 (1996).
Portman et al., "Genitourinary syndrome of menopause: new terminology for vulvovaginal atrophy from the International Society for the Study of Women's Sexual Health and the North American Menopause Society," (2014) Menopause, vol. 21(10), pp. 1063-1068.
Proctor and Farquhar: "Dysmenorrhoea", Clin Evid, 9, p. 1994-2013 (2003).
Reactivity Chart 1: Protection for Hydroxyl Group: Ethers. In Greene's Protective Groups in Organic Synthesis, (1999) 3E, pp. 708-711.
Rodstrom et al., "A longitudinal study of the treatment of 25 hot flushes: the population study of women in Gothenburg during a quarter of a century," (2002) Menopause, vol. 9(3), pp. 156-161.
Rosenbaum et al., Inhibition of ovulation by a novel progestogen (drospirenone) alone or in combination with ethinylestradiol, Euro. J. Contracept. & Repro. Health Care, 5(1):14-24 (2000).
Rosing et al., "Oral contraceptives and venous thrombosis: different sensitivities to activated protein C in women using second- and third-generation oral contraceptives", Br J Haematol., 97(1), p. 233-238.
Sakakibara, et al. "Syntheses of (14beta, 17alpha)-14-Hydroxy-and(14beta,17alpha)-2,14-Dihydroxyestradiols and Their Activities", Biosci. Biotech. Biochem, (1996), vol. 60, No. 3, pp. 411-414.
Santoro, "Symptoms of menopause: hot flushes," (2008) Clin Obstet Gynecol, vol. 51(3), pp. 539-548.
Savjani et al, "Drug solubility: importance and enhancement techniques", ISRN Pharm., 2012: 195727.
Shulman, "Estelle, Estetrol: changing hormones in advancing oral contraception," Presented at Eur. Soc. Contraception & Reprod. Health, 14th Cong, 2nd Global Conf. (May 5, 2016).
Sidney et al: "Recent combined hormonal contraceptives (CHCs) and the risk of thromboembolism and other cardiovascular events in new users", Contraception, 87(1), p. 93-100 (2013).
Simon et al., "Menopausal hormone therapy for vasomotor symptoms: balancing the risks and benefits with ultra-low doses of estrogen," (2007) Expert Opin Investig Drugs, vol. 16(12), pp. 2005-2020.
Simoni, et al. "The Discovery of Estrone, Estriol, and Estradiol and the Biochemical Study of Reproduction. The Work of Edward Adelbert Doisy", J. Biol. Chem (2002), vol. 277, No. 28, e17.
Spitzer et al: "Third generation oral contraceptives and risk of venous thromboembolic disorders: an international case-control study. Transnational Research Group on Oral Contraceptives and the Health of Young Women", BMJ, 312(7023), p. 83-88 (1996).
Strowitzki et al., "Efficacy of ethinylestradiol 20 ?g/drospirenone 3 mg in a flexible extended reimen in women with moderate-to-severe primary dysmenorrhea: an open-label, multicenter, ramdomised, controlled study," J. Fam. Plann. Reprod. Health Care (2012) vol. 38, pp. 94-101.
Sundell et al, "Factors influencing the prevalence and severity of dysmenorrhoea in young women.", Br J Obstet Gynaecol, 97(7), p. 588-594.
Takahaski et al. Tetrahedron Letters, vol. 25, pp. 1921-1924 (1984).
Takahaski et al. Tetrahedron, vol. 41, pp. 5747-5754 (1985).
Takeuchi et al. Bull. Chem. Soc. Jpn., vol. 74, pp. 363-370 (2001).
Tchaicovski and Rosing: "Mechanisms of estrogen-induced venous thromboembolism", Thromb Res., 126(1):5-11.
Trost et al., J. Org. Chem, vol. 58, No. 6, pp. 1579-1581 (1993).
Egner et aL. Tetrahedron, vol. 55, pp. 11267-11274 (1999).
Utian et al., "Comparative controlled trial of a novel oral estrogen therapy, estradiol acetate, for relief of menopause symptoms," (2005) Menopause, vol. 12(6), pp. 708-715.
Visser et al., "Clinical applications for estetrol," Journal of Steroid Biochemistry and Molecular Biology 114 (2009) 85-59.
Vlieg et al: "The venous thrombotic risk of oral contraceptives, effects of oestrogen dose and progestogen type: results of the MEGA case-control study", BMJ, 339:b2921 (2009).
Wang et al. Tetrahedron, vol. 63, pp. 7977-7984 (2007).
Warmerdam et al Climateric, vol. 11, No. suppl. 1, pp. 59-63 (2008).
Williams et al., "Strategies to address low drug solubility in discovery and development," (2013) Pharmacological Reviews, vol. 65(1), pp. 416-445.
Winkler et al, "Cycle control, quality of life and acne with two low-dose oral contraceptives containing 20 microg ethinylestradiol", Contraception, 96(6), p. 469-476.

(56) References Cited

OTHER PUBLICATIONS

Wong et al "Oral contraceptive pill as treatment for pirmary dysmenorrhoea", Cochrane Database Syst Rev., CD002120.
WTO: "Venous thromboembolic disease and combined oral contraceptives: results of international multicentre case-control study", Lancet, 346(8990): p. 1575-1582 (1995).
Ylikorkala et al., "New concepts in dysmenorrhea", Am J Obstet Gynecol, 130(7), p. 833-847.
Zhang et al., Efficacy of minor analgesics in primary dysmenorrhoea: a systematic review.
Liu et al., J. Org. Chem., vol. 61, pp. 6693-6699 (1996).

\* cited by examiner

*Scheme 1*

*Scheme 2*

*Scheme 3*

*Scheme 4*

Scheme 6

*Scheme 7*

Scheme 8

*Scheme 9*

*Scheme 10*

*Scheme 11*

PROCESS FOR THE PREPARATION OF ESTETROL

CROSS-REFERENCE TO RELATED APPLICATIONS

This application is Continuation Application of U.S. patent application Ser. No. 14/233,362, filed Apr. 3, 2014, which is now abandoned, and which is the National Phase of International Patent Application No. PCT/NL2012/050514, filed Jul. 18, 2012, published on Jan. 24, 2013 as WO 2013/012328 A1, which claims priority to U.S. Provisional Application No. 61/509,168, filed Jul. 19, 2011 and European Patent Application No. 11174509.7, filed Jul. 19, 2011. The contents of these applications are herein incorporated by reference in their entirety.

TECHNICAL FIELD OF THE INVENTION

The present invention relates to a process for the preparation of estra-1,3,5(10)-trien-3,15α,16α,17β-tetraol (estetrol), starting from estrone. The invention further relates to a process for the preparation of 3-A-oxy-estra-1,3,5(10),15-tetraen-17-one, starting from estrone, via the corresponding silyl enol ether 17-B-oxy-3-A-oxy-estra-1,3,5(10),16-tetraene, wherein A is a protecting group and B is —Si($R^2$)$_3$.

BACKGROUND OF THE INVENTION

Estrogenic substances are commonly used in methods of Hormone Replacement Therapy (HRT) and in methods of female contraception. These estrogenic substances can be divided in natural estrogens and synthetic estrogens. Examples of natural estrogens that have found pharmaceutical application include estradiol, estrone, estriol and conjugated equine estrogens. Examples of synthetic estrogens, which offer the advantage of high oral bioavailability, include ethinyl estradiol and mestranol.

Estetrol has been found effective as an estrogenic substance for use in HRT, as is disclosed in WO 02/094276. Estetrol is a biogenic estrogen that is endogeneously produced by the fetal liver during human pregnancy. Other important applications of estetrol are in the fields of contraception, therapy of auto-immune diseases, prevention and therapy of breast and colon tumors, enhancement of libido, skin care, and wound healing as described in WO 02/094276, WO 02/094279, WO 02/094278, WO 02/094275, WO 03/041718 and WO 03/018026.

The structural formula of estetrol [estra-1,3,5(10)-trien-3,15α,16α,17β-tetraol] I is shown below. In this description the IUPAC-recommended ring lettering and atom numbering for steroids and steroid derivatives, as depicted below, are applied.

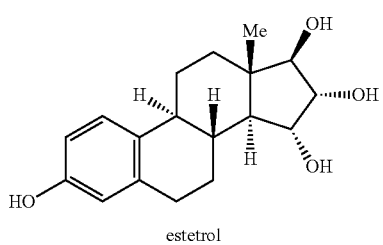

estetrol

I

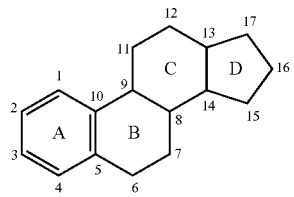

The synthesis of estetrol on a laboratory scale is for example disclosed in Fishman et al., *J. Org. Chem.* 1968, 33, 3133-3135, wherein estetrol is synthesised from estrone derivative III as shown in Scheme 1 in FIG. 1 (numbering according to Fishman et al.).

Fishman et al. prepared estrone derivative III according to the procedure disclosed by Cantrall et al., *J. Org. Chem.* 1964, 29, 214-217 and Johnson et al., *J. Am. Chem. Soc.* 1957, 79, 2005-2009, as described in more detail below. The overall yield of the 3-step process shown in Scheme 1 is, starting from estrone derivative III, about 7%.

Another synthesis of estetrol wherein estrone is the starting material is disclosed in Nambara et al., *Steroids* 1976, 27, 111-121. This synthesis is shown in Scheme 2 in FIG. 2 (numbering according to Nambara et al.). The carbonyl group of estrone I is first protected by treatment with ethylene glycol and pyridine hydrochloride followed by acetylation of the hydroxyl group at $C_3$. The next sequence of steps involved a bromination/base catalyzed dehydrobromination resulting into the formation of 17,17-ethylenedioxyestra-1,3,5(10),15-tetraene-3-ol (compound IVa). This compound IVa was subsequently acetylated which produced 17,17-ethylenedioxyestra-1,3,5(10),15-tetraene-3-ol-3-acetate (compound IVb). In a next step, the dioxolane group of compound IVb was hydrolysed by using p-toluene sulfonic acid to compound Vb, followed subsequently by reduction of the carbonyl group at $C_{17}$ (compound Vc) and oxidation of the double bond of ring D thereby forming estra-1,3,5(10)-triene-3,15α,16α,17β-tetraol-3,17-diacetate (compound VIb).

Suzuki et al., *Steroids* 1995, 60, 277-284 also discloses the synthesis of estetrol by using compound Vb of Nambara et al. as starting material. The carbonyl group at $C_{17}$ of this compound was first reduced followed by acetylation yielding estra-1,3,5(10),15-tetraene-3,17-diol-3,17-diacetate (compound 2b). The latter was subjected to oxidation with $OsO_4$ which provided estra-1,3,5(10)-triene-3,15α,16α,17β-tetraol-3,17-diacetate (compound 3b) in 46% yield.

According to Nambara et al. and Suzuki et al., the synthesis of estetrol can be performed with a yield of approximately 8%, starting from estrone.

The synthesis of estrone derivative VI starting from estrone is disclosed by Cantrall et al., *J. Org. Chem.* 1964, 29, 214-217 and 64-68, and by Johnson et al., *J. Am. Chem. Soc.* 1957, 79, 2005-2009, and is shown in Scheme 3 in FIG. 3 (numbering according to Johnson et al.).

The synthetic route depicted in Scheme 3 was also applied by Poirier et al., *Tetrahedron* 1991, 47, 7751-7766 for the synthesis of an analogue of compound VI wherein a benzyl ether is present on the 3-position instead of the methyl ether in VI.

Another method to prepare estrone derivative VI of Scheme 3, wherein the hydroxyl group on the 3-position of estrone is protected as a methyl ether, is disclosed in Li et al., *Steroids* 2010, 75, 859-869, and is shown in Scheme 4 in FIG. 4 (numbering according to Li et al.). After protection of the 3-OH group of estrone 39 as the methyl ether to form 40, the keto function on $C_{17}$ is converted into trimethylsilyl enol ether 41. Compound 41 is then converted into 42 (corresponding to estrone derivative VI of Scheme 3) in the presence of 1 equivalent of palladium(II) acetate, Pd(OAc)$_2$. According to Li et al. 42 is obtained in three steps in a yield of about 60%, starting from estrone.

The method shown in Scheme 4 for the preparation of 42 in the presence of 1 equivalent of Pd(OAc)$_2$ is also disclosed in Smith et al., *Org. Lett.* 2006, 8, 2167-2170, Smith et al., *J. Org. Chem.* 2007, 72, 4611-4620 and Bull et al., *J. Chem. Soc., Perkin Trans.* 1, 2000, 1003-1013.

Said method is not applied in a total synthesis of estetrol I.

In order to get a high conversion and an acceptable yield of 42, one equivalent of Pd(OAc)$_2$, with respect to 41, needs to be employed. Due to the high cost of palladium, application of this method is therefore not desirable for a process that is executed on an industrial scale.

A method for the preparation of enones using hypervalent iodine(V) species is disclosed by Nicolaou et al., *Angew. Chem.* 2002, 114, 1038-1042. Various ketones are converted into α, β-unsaturated enones via oxidation of the corresponding trimethylsilyl enol ethers, induced by o-iodoxybenzoic acid (IBX) or IBX complexed to an N-oxide ligand such as 4-methoxypyridine-N-oxide (IBX.MPO).

One of the examples with a more complex molecule that is disclosed by Nicolaou et al. is the conversion of steroid derivative 27 into α,β-unsaturated 28 in 62% yield (Scheme 5, numbering according to Nicolaou et al.).

Scheme 5

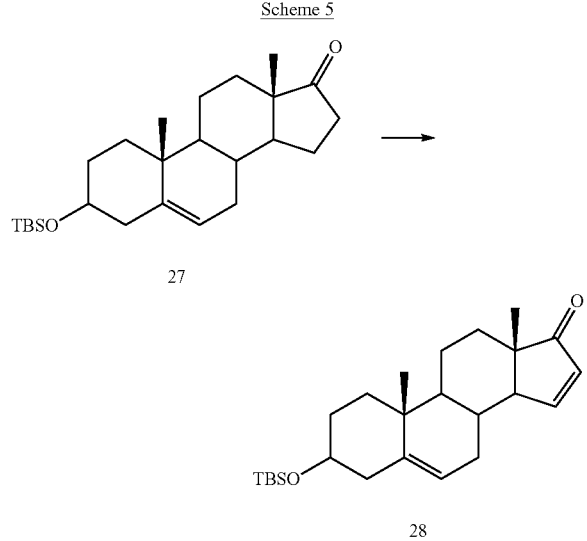

The method disclosed by Nicolaou et al. is not employed in the preparation of estrone derivatives such as compound III of Scheme 1, compound Vb of Scheme 2, compound VI of Scheme 3 or compound 42 of Scheme 4, nor in the preparation of estetrol I.

Another iodine(V) species, 2-iodoxybenzenesulphonic acid (IBS) was disclosed recently in EP 2085373 and in Yamada et al., *Spec. Chem. Mag.* 2011, 31, 18-20. The structure of both IBX and IBS is shown below.

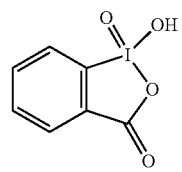

IBX

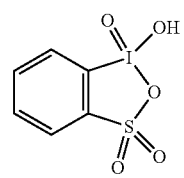

IBS

Yamada et al. discloses the use of IBS, in a catalytic amount, for the conversion of several cyclic alcohols with a relatively simple structure such as cyclopentanol and (optionally substituted) cyclohexanol into α,β-unsaturated enones. The use of IBS for the conversion of complex molecules such as steroids into α,β-unsaturated enone derivatives is not disclosed in Yamada et al. or in EP 2085373.

A process for the preparation of estetrol that is suitable for the preparation of estetrol on an industrial scale is disclosed in WO 2004/041839. This process is shown in Scheme 6 in FIG. 5 (numbering according to WO 2004/041839), and comprises the following steps:
(1) converting estrone (7) into 3-A-oxy-estra-1,3,5(10), 15-tetraen-17-one (6), wherein A is a protecting group;
(2) reduction of the 17-keto group of 3-A-oxy-estra-1,3, 5(10),15-tetraen-17-one (6) to 3-A-oxy-estra-1,3,5(10), 15-tetraen-17β-ol (5);
(3) protection of the 17-OH group of 3-A-oxy-estra-1,3, 5(10),15-tetraen-17β-ol (5) to 3-A-oxy-17-C-oxy-estra-1,3,5(10),15-tetraene (4), wherein C is a protecting group;
(4) oxidizing the carbon-carbon double bond of ring D of 3-A-oxy-17-C-oxy-estra-1,3,5(10),15-tetraene (4) to protected estetrol (3); and
(5) removing the protecting groups, wherein preferably protecting group A is removed first to form 17-OC protected estetrol (2) and subsequently protecting group C is removed to form estetrol (1);
wherein the protecting group A is selected from an $C_1$-$C_5$ alkyl group or a $C_7$-$C_{12}$ benzylic group and the protecting group C is selected from monofunctional aliphatic hydroxyl protecting groups.

Step (1) of this process, the preparation of 3-A-oxy-estra-1,3,5(10),15-tetraen-17-one (6) starting from estrone (7), is shown in Scheme 7 and comprises the following steps:
(1a) conversion of the 3-OH group of estrone (7) into a 3-AO group to form 3-A-oxy-estra-1,3,5(10)-trien-17-one (8);
(1b) conversion of the 17-keto group of 3-A-oxy-estra-1, 3,5(10)-trien-17-one (8) into a protected keto group to form 3-A-oxy-17-D-estra-1,3,5(10)-triene (9);
(1c) halogenation of $C_{16}$ of 3-A-oxy-17-D-estra-1,3,5 (10)-triene (9) to form 3-A-oxy-16-X-17-D-estra-1,3,5 (10)-triene (10) wherein X is a halogen atom selected from the group chloride, bromide and iodide and wherein X is preferably bromide;
(1d) dehalogenation of 3-A-oxy-16-X-17-D-estra-1,3,5 (10)-triene (10) to 3-A-oxy-17-D-estra-1,3,5(10),15-tetraene (11); and (1e) deprotection of the protected keto group of 3-A-oxy-17-D-estra-1,3,5(10),15-tetraene (11) to form 3-A-oxy-estra-1,3,5(10),15-tetraen-17-one (6), wherein A is selected from an $C_1$-$C_5$ alkyl group, preferably a methyl group, or a $C_7$-$C_{12}$ benzylic group, preferably a benzyl group, and wherein D is ethylene dioxy.

With the method as disclosed in WO 2004/041839 and shown in Schemes 6 and 7 in FIG. 5 and FIG. 6, respectively, estetrol is obtained in an overall yield of 10.8%, starting from estrone.

Although the process disclosed in WO 2004/041839 is suitable for an industrial scale preparation of estetrol 1, and although estetrol is obtained with a reasonable overall yield, the process still suffers from several disadvantages. For example, the conversion of 7 into 6 is performed in a total of 5 steps. Isolation and purification of each intermediate product inevitably results in a loss of yield, thereby reducing the overall yield of estetrol. Furthermore, the conversion of 7 into 6 involves a halogenation (step 1c) and a dehalogenation step (step 1d), typically a bromination and a debromination step. In particular during said halogenation and dehalogenation reactions, various side products are produced. Since these side products need to be removed from the intermediate products, an extensive amount of purification of the intermediate products is required, resulting in a substantial loss of yield of the intermediate products, and therefore, ultimately, in a substantial loss in the overall yield of estetrol.

It is an object of the present invention to provide a process for the preparation of estetrol that is suitable for the production of estetrol on an industrial scale, wherein estetrol is preferably obtained in a high purity and in a good yield. Also, there is a need for a process for the preparation of estetrol wherein the formation of side products is minimal, i.e. as low as possible. Particularly, there is a need for a process for the preparation of estetrol wherein the halogenation and subsequent dehalogenation reactions of the process as disclosed in WO 2004/041839 are omitted.

SUMMARY OF THE INVENTION

The present invention relates to a process for the preparation of estra-1,3,5(10)-trien-3,15α,16α,17β-tetraol I which comprises the steps of:
(1) conversion of estrone II into 17-B-oxy-3-A-oxy-estra-1,3,5(10),16-tetraene III, wherein A is a protecting group and B is —$Si(R^2)_3$;
(2) conversion of 17-B-oxy-3-A-oxy-estra-1,3,5(10),16-tetraene III into 3-A-oxy-estra-1,3,5(10),15-tetraen-17-one IV, wherein A is a protecting group;
(3) reduction of the 17-keto group of 3-A-oxy-estra-1,3,5(10),15-tetraen-17-one IV to form 3-A-oxy-estra-1,3,5(10),15-tetraen-17β-ol V, wherein A is a protecting group;
(4) protection of the 17-OH group of 3-A-oxy-estra-1,3,5(10),15-tetraen-17β-ol V to form 3-A-oxy-17-C-oxy-estra-1,3,5(10),15-tetraene (VI), wherein A and C are protecting groups;
(5) oxidation of the carbon-carbon double bond of ring D of 3-A-oxy-17-C-oxy-estra-1,3,5(10), 15-tetraene (VI) to form protected estetrol VII, wherein A and C are protecting groups; and
(6) removal of protecting groups A and C to form estetrol I;

wherein:
A is a protecting group selected from the group consisting of a $C_1$-$C_5$ alkyl group, a $C_7$-$C_{12}$ benzylic group and a —$Si(R^1)_3$ group, wherein $R^1$ is independently selected from the group consisting of a $C_1$-$C_6$ alkyl group and a $C_6$-$C_{12}$ aryl group;
B is —$Si(R^2)_3$, wherein $R^2$ is independently selected from the group consisting of a $C_1$-$C_6$ alkyl group and a $C_6$-$C_{12}$ aryl group; and
C is a protecting group selected from the group consisting of monofunctional aliphatic hydroxyl protecting groups.

This process is shown in Scheme 8 in FIG. 7.

The invention further relates to a process for the synthesis of 3-A-oxy-estra-1,3,5(10),15-tetraen-17-one IV, wherein A is a protecting group, which comprises the steps of:
(1) conversion of estrone II into 17-B-oxy-3-A-oxy-estra-1,3,5(10),16-tetraene III, wherein A is a protecting group and B is —$Si(R^2)_3$; and
(2) conversion of 17-B-oxy-3-A-oxy-estra-1,3,5(10),16-tetraene III into 3-A-oxy-estra-1,3,5(10),15-tetraen-17-one IV, wherein A is a protecting group, wherein said conversion of III into IV is performed in the presence of an iodine(V) species, and wherein the iodine(V) species is present in an amount of about 0.1 mol % or more with respect to compound III;

wherein:
A is a protecting group selected from the group consisting of a $C_1$-$C_5$ alkyl group, a $C_7$-$C_{12}$ benzylic group and a —$Si(R^1)_3$ group, wherein $R^1$ is independently selected from the group consisting of a $C_1$-$C_6$ alkyl group and a $C_6$-$C_{12}$ aryl group; and
B is —$Si(R^2)_3$, wherein $R^2$ is independently selected from the group consisting of a $C_1$-$C_6$ alkyl group and a $C_6$-$C_{12}$ aryl group.

This process is shown in Scheme 11 in FIG. 10.

DETAILED DESCRIPTION OF THE INVENTION

Figure 1:
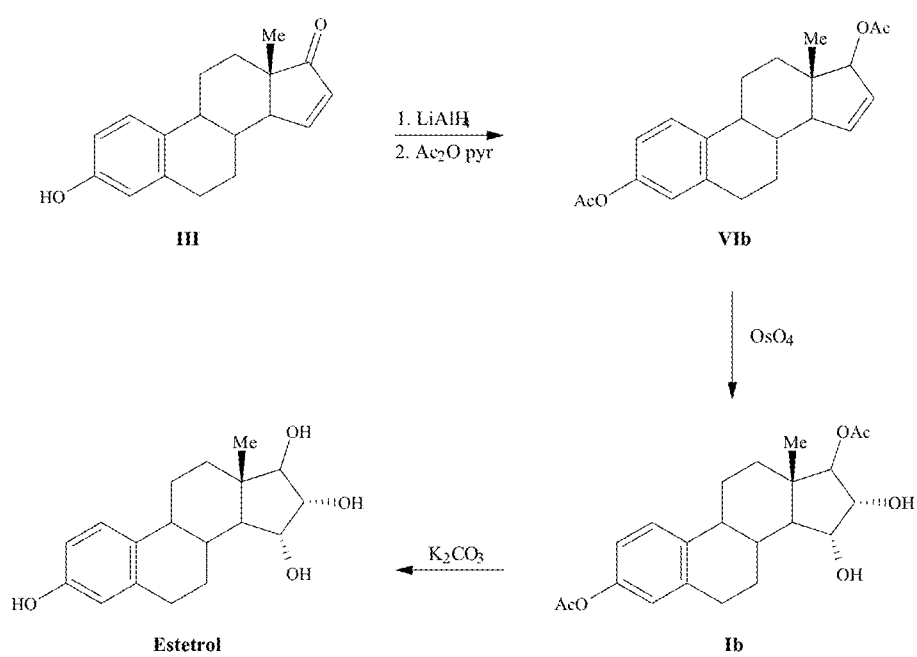
FIG. 1. Scheme 1 depicting the synthesis of estetrol from estrone derivative III disclosed in Fishman et al., *J. Org. Chem.* 1968, 33, 3133-3135 (numbering according to Fishman et al.).
Figure 2:
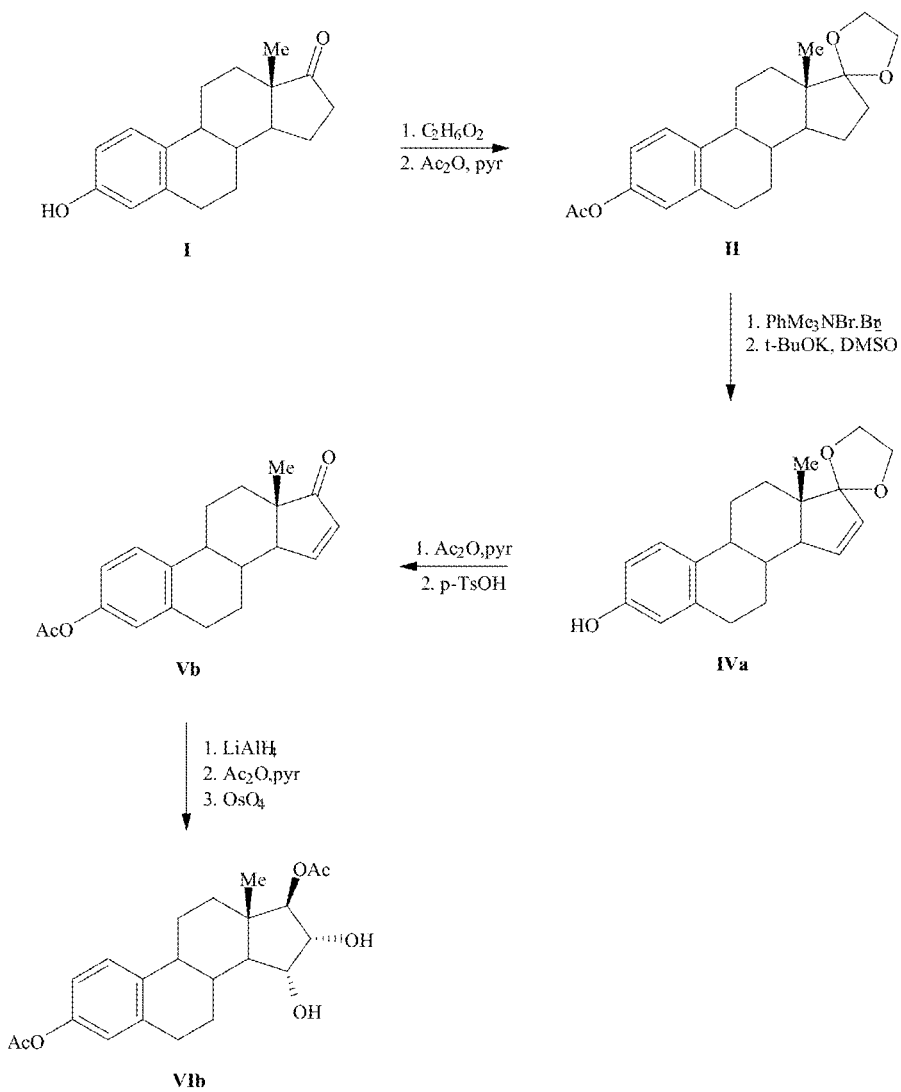
FIG. 2. Scheme 2 depicting the synthesis of estetrol disclosed in Nambara et al., *Steroids* 1976, 27, 111-121 (numbering according to Nambara et al.).
Figure 3:
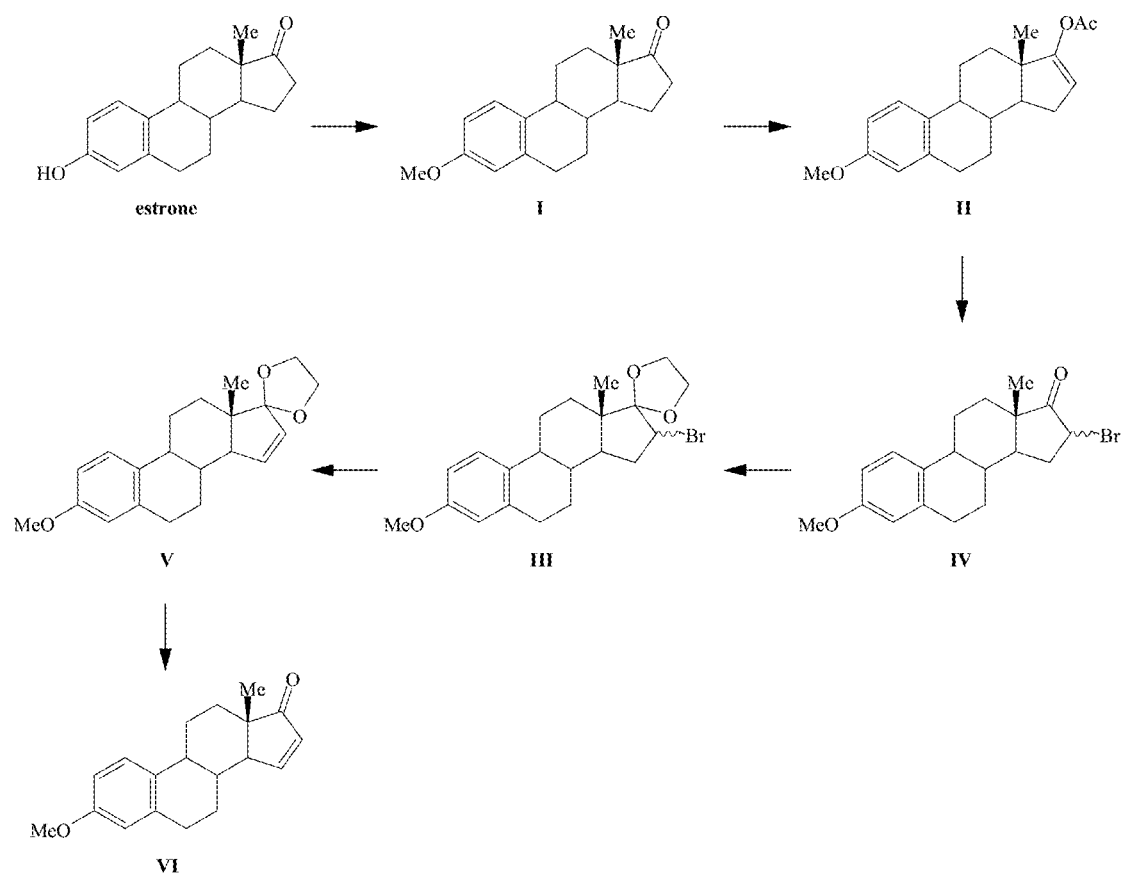
FIG. 3. Scheme 3 depicting the synthesis of estrone derivative VI disclosed in Cantrall et al., *J. Org. Chem.* 1964, 29, 214-217 and 64-68, and in Johnson et al., *J. Am. Chem. Soc.* 1957, 79, 2005-2009 (numbering according to Johnson et al.).
Figure 4:
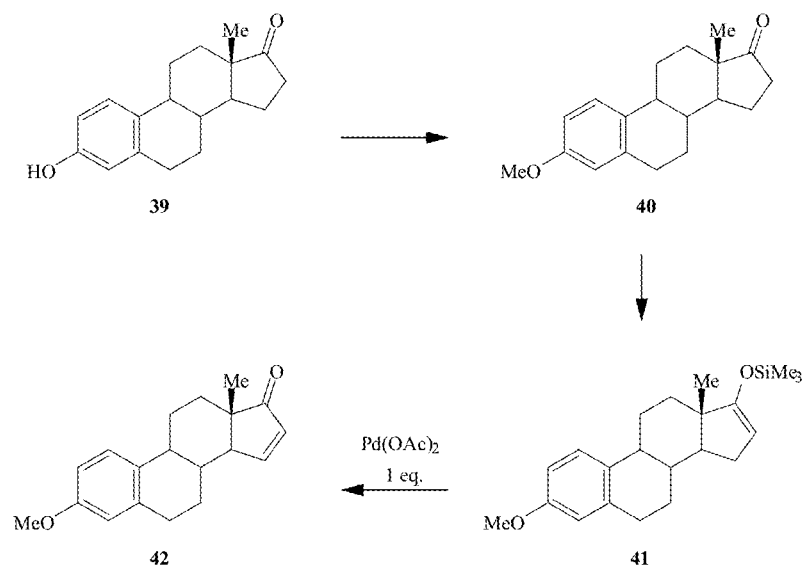
FIG. 4. Scheme 4 depicting the synthesis of estrone as disclosed in Li et al., *Steroids* 2010, 75, 859-869 (numbering according to Li et al.).
Figure 5:
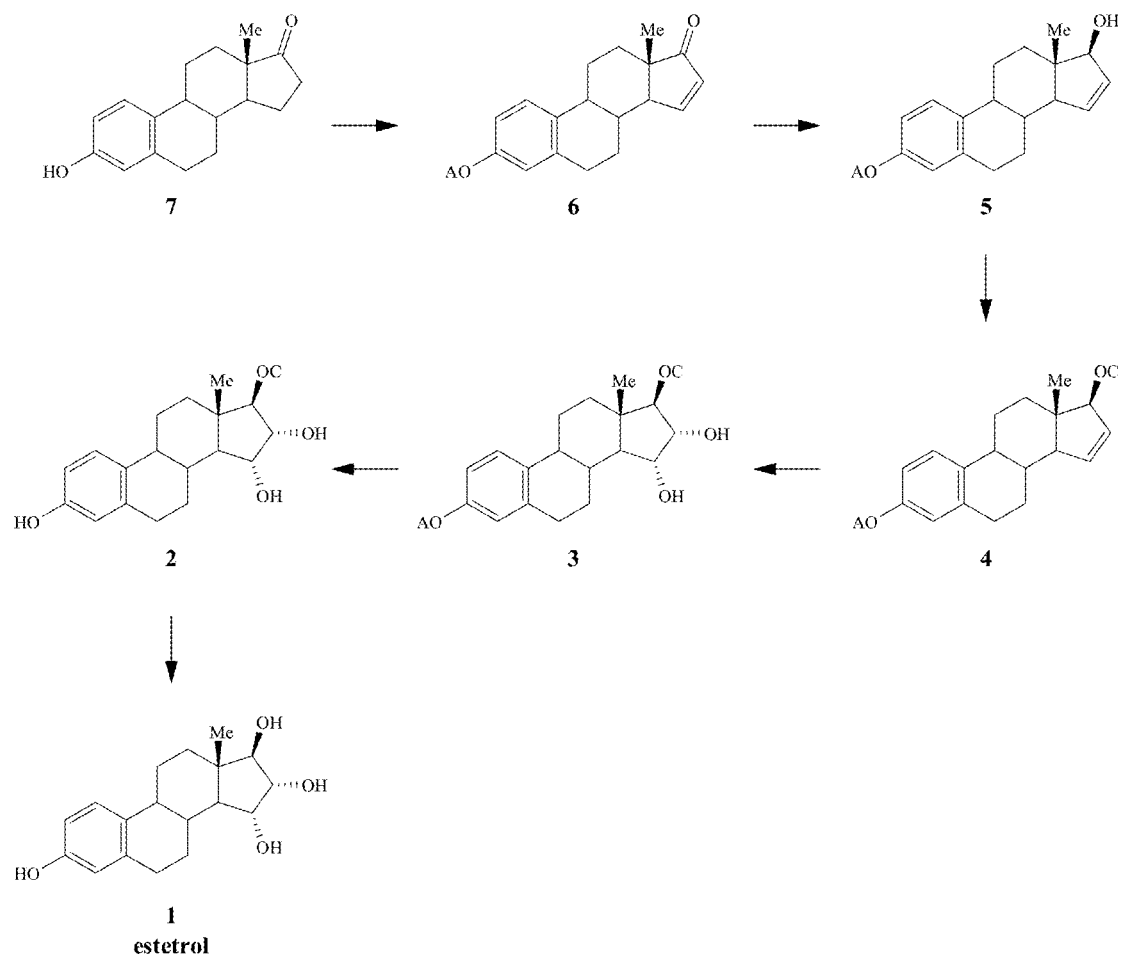
FIG. 5. Scheme 6 depicting the process for the preparation of estetrol disclosed in WO 2004/041839 (numbering according to WO 2004/041839).
Figure 6:
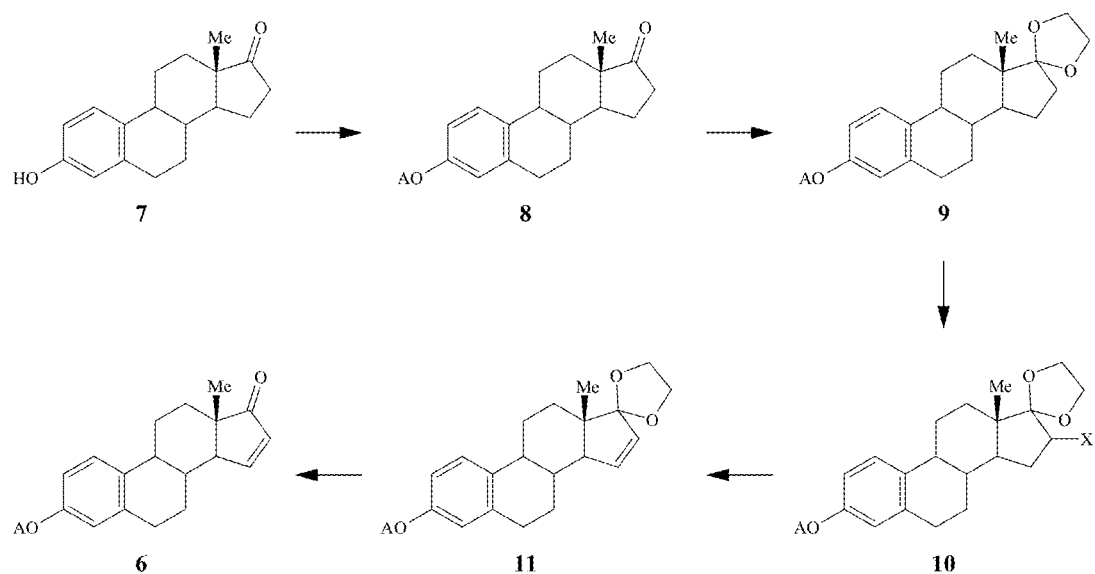
FIG. 6. Scheme 7 depicting the synthesis of 3-A-oxy-estra-1,3,5(10),15-tetraen-17-one 6 starting from estrone (7).

The verb "to comprise" and its conjugations as used in this description and in the claims are used in their non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

In this patent application the term "alkyl" includes linear, branched and cyclic alkyl groups such as for example methyl, ethyl, n-propyl, i-propyl, cyclopropyl, n-butyl, s-butyl, t-butyl, cyclobutyl, n-pentyl, s-pentyl, t-pentyl, cyclopentyl, methylcyclobutyl and cyclohexyl.

A benzyl group is defined as a —$CH_2(C_6H_5)$ group.

A $C_7$-$C_{12}$ benzylic group is defined as a benzyl group, i.e. a —$CH_2(C_6H_5)$ group as defined above, or a benzyl group that is substituted with one or more substituents at the ortho, meta and/or para position of the aromatic nucleus, wherein the substituents are aliphatic groups, optionally substituted by one or more heteroatoms and/or halogen atoms that do not adversely interfere with the synthetic process. Examples of a substituted benzyl group include —$CH_2(C_6H_4Me)$ or —$CH_2(C_6H_3Me_2)$, wherein Me is defined as a methyl group (—$CH_3$).

A $C_6$-$C_{12}$ aryl group is defined as a monocyclic, bicyclic or polycyclic structure comprising 6 to 12 carbon atoms. Optionally, the aryl groups may be substituted by one or more substituents at the ortho, meta and/or para position of the aromatic nucleus, wherein the substituents are aliphatic groups, optionally substituted by one or more heteroatoms and/or halogen atoms that do not adversely interfere with the synthetic process. Examples of an aryl group include phenyl, p-tolyl, mesityl and naphthyl.

As is obvious to a person skilled in the art, the alkyl and benzylic groups and the —$Si(R^1)_3$ groups are intended as a protecting group and these groups must therefore be relatively easy to add and relatively easy to remove under conditions that have substantially no adverse effect on the molecular structure of the estrone derived steroid molecules.

Figure 7:
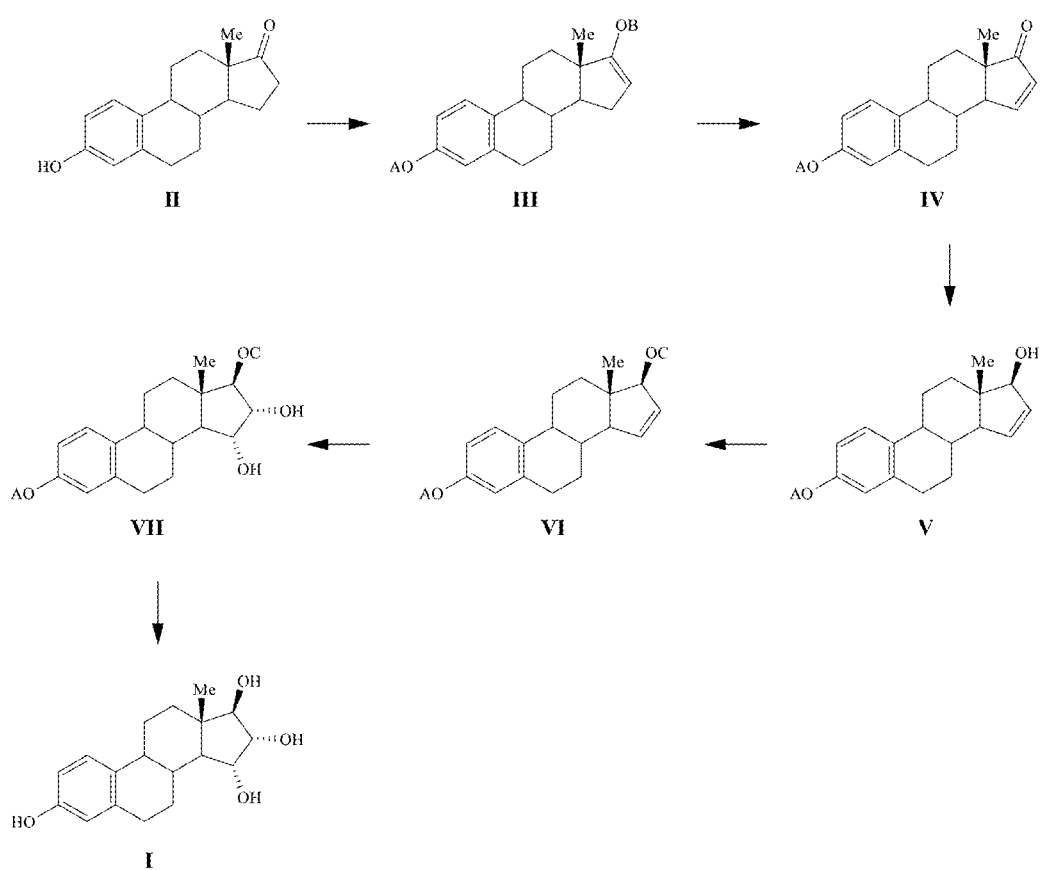
FIG. 7. Scheme 8 depicting the process for the preparation of estra-1,3,5(10)-trien-3,15α,16α,17β-tetraol I (estetrol) according to the present invention.
Figure 8:
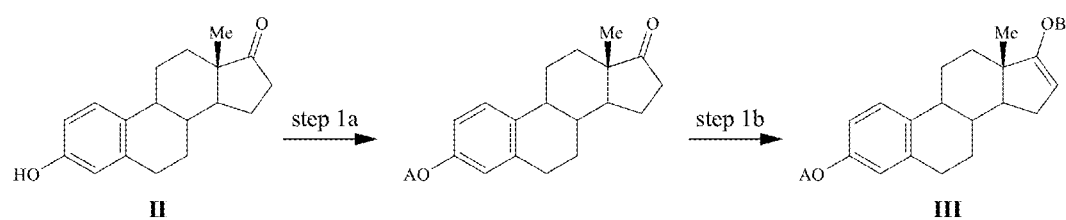
FIG. 8. Scheme 9 depicting the conversion of estrone II into 17-B-oxy-3-A-oxy-estra-1,3,5(10),16-tetraene III.

The present invention relates to a process for the preparation of estra-1,3,5(10)-trien-3,15α,16α,17β-tetraol I (estetrol) which comprises the steps of:

(1) conversion of estrone II into 17-B-oxy-3-A-oxy-estra-1,3,5(10),16-tetraene III, wherein A is a protecting group and B is —$Si(R^2)_3$;
(2) conversion of 17-B-oxy-3-A-oxy-estra-1,3,5(10),16-tetraene III into 3-A-oxy-estra-1,3,5(10),15-tetraen-17-one IV, wherein A is a protecting group;
(3) reduction of the 17-keto group of 3-A-oxy-estra-1,3,5(10),15-tetraen-17-one IV to form 3-A-oxy-estra-1,3,5(10),15-tetraen-17β-ol V, wherein A is a protecting group;
(4) protection of the 17-OH group of 3-A-oxy-estra-1,3,5(10),15-tetraen-17β-ol V to form 3-A-oxy-17-C-oxy-estra-1,3,5(10),15-tetraene VI, wherein A and C are protecting groups;
(5) oxidation of the carbon-carbon double bond of ring D of 3-A-oxy-17-C-oxy-estra-1,3,5(10),15-tetraene VI to form protected estetrol VII, wherein A and C are protecting groups; and
(6) removal of protecting groups A and C to form estetrol I;

wherein A is a protecting group selected from the group consisting of a $C_1$-$C_5$ alkyl group, a $C_7$-$C_{12}$ benzylic group and a —$Si(R^1)_3$ group, wherein $R^1$ is independently selected from the group consisting of a $C_1$-$C_6$ alkyl group and a $C_6$-$C_{12}$ aryl group; B is —$Si(R^2)_3$, wherein $R^2$ is independently selected from the group consisting of a $C_1$-$C_6$ alkyl group and a $C_6$-$C_{12}$ aryl group; and C is a protecting group selected from the group consisting of monofunctional aliphatic hydroxyl protecting groups, i.e. a monofunctional protecting group that is suitable for the protection of an aliphatic hydroxyl group. The process according to the invention is depicted in Scheme 8 shown in FIG. 7.

Step (1): Conversion of estrone II into 17-B-oxy-3-A-oxy-estra-1,3,5(10),16-tetraene III, wherein A is a protecting group and B is —$Si(R^2)_3$ Step 1 of the process comprises the steps of (1a) the protection of the hydroxyl group on the 3-position of estrone II with a protecting group A, and (1b) the conversion of the keto functionality on the 17-position into the corresponding silyl enol ether.

In a preferred embodiment, step (1a) is executed first, followed by step (1b), in other words, the 3-hydroxyl group of estrone II is first protected with a protecting group A, followed by the conversion of the thus obtained 3-protected estrone into the corresponding 3-protected silyl enol ether III, as is shown in Scheme 9. Alternatively, and more preferably, step (1a) and (1b) may be executed simultaneously, or in a "two-reactions-one-pot" procedure.

Step (1a): Protection of the 3-OH-Group

Step (1a) relates to the protection of the 3-hydroxyl group of estrone II with a protecting group A. Protecting group A is selected from the group consisting of a $C_1$-$C_5$ alkyl group, a $C_7$-$C_{12}$ benzylic group and a —$Si(R^1)_3$ group, wherein $R^1$ is independently selected from the group consisting of a $C_1$-$C_6$ alkyl group and a $C_6$-$C_{12}$ aryl group.

When protecting group A is a $C_1$-$C_5$ alkyl group, A may for example be methyl, ethyl, propyl, iso-propyl (i-propyl), butyl, iso-butyl (i-butyl) or tertiair butyl (t-butyl). Preferably, if A is a $C_1$-$C_5$ alkyl group, A is methyl.

When A is a $C_7$-$C_{12}$ benzylic group, it is preferred that A is a benzyl group, —$CH_2(C_6H_5)$. However, the $C_7$-$C_{12}$ benzylic group may also be a substituted benzyl group, such as for example —$CH_2(C_6H_3Me_2)$. Most preferably, A is a benzyl group.

When A is a —$Si(R^1)_3$ group each $R_1$ group is independently selected, in other words, each of the three $R^1$ groups within one —$Si(R^1)_3$ group may be different from the others. Preferably, $R^1$ is selected from the group consisting of methyl, ethyl, propyl, propyl, butyl, i-butyl, t-butyl, phenyl, p-tolyl and mesityl. Examples of suitable —$Si(R^1)_3$ groups include trimethylsilyl (TMS), triethylsilyl (TES), diethylisopropylsilyl (DEIPS), isopropyldimethylsilyl (IPDMS), tri-isopropylsilyl (TIPS), t-butyldimethylsilyl (TBDMS) and t-butyldiphenylsilyl (TBDPS). Preferably, when A is a —$Si(R^1)_3$ group, the —$Si(R^1)_3$ group is a sterically hindered ("bulky") —$Si(R^1)_3$ group such as for example a DEIPS, IPDMS, TIPS, TBDMS or TBDPS group.

The protection of the hydroxyl group on $C_3$ by alkylation is typically carried out by reacting estrone with a component selected from an alkylating reagent, preferably a $C_1$-$C_5$ alkyl halogenide, preferably a methyl halogenide, or a $C_7$-$C_{12}$ benzylic halogenide, preferably benzyl halogenide. Preferably, the halogen atom of the alkylating agent is bromide, chloride or iodide, most preferably bromide or iodide. According to the present invention, the most preferred alkylating agent is benzyl bromide or methyl iodide, wherein benzyl bromide is more preferred than methyl iodide. However, it is also possible to use a dialkyl sulphate instead of a $C_1$-$C_5$ alkyl halogenide, wherein the alkyl groups contain 1-5 carbon atoms and wherein the alkyl groups are preferably methyl (i.e. the preferred dialkyl sulphate is then dimethyl sulphate).

The protection of the 3-OH group by silylation is typically carried out by reacting estrone with a silylation reagent, such as for example a silyl chloride, a silyl iodide or a silyl triflate, in the presence of a base, for example an amine base.

The protection of the 3-OH group is typically executed in the presence of a base. Suitable bases are known to a person skilled in the art, and include for example potassium bases such as potassium carbonate ($K_2CO_3$), potassium t-butoxide (KOtBu), potassium hexamethyldisilazide (KHMDS) or potassium hydride (KH), sodium bases such as sodium methoxide (NaOMe), sodium t-butoxide (NaOtBu), sodium hexamethyldisilazide (NaHMDS) or sodium hydride (NaH), lithium bases such as lithium diisopropylamide (LDA), lithium tetramethylpiperidide (LiTMP) or lithium hexamethyldisilazide (LiHMDS), amine bases such as triethyl amine ($Et_3N$), tetramethylethylene diamine (TMEDA), 1,8-diazabicyclo[5.4.0]undec-7-ene (DBU), 1,5-diazabicyclo[4.3.0]non-5-ene (DBN), imidazole and 2,6-lutidine, and the like.

As will be clear to a person skilled in the art, the type of base that is preferred in a specific reaction depends strongly on the type of alkylating or silylation reagent used in said reaction. When for example the 3-OH group is protected via an alkylation reaction, e.g. with benzyl bromide as alkylating reagent, then the use of an amine base in that reaction is less preferred. When the 3-OH group is protected via a silylation reaction, then the use of a small alkoxide, such as for example NaOMe, as a base is less preferred.

Suitable solvents for the protection reaction are known to the person skilled in the art, and include for example dimethylformamide (DMF), dichloromethane (DCM), ethyl acetate (EtOAc), toluene, acetonitrile (MeCN), dimethyl sulfoxide (DMSO), dimethylacetamide, dimethyl carbonate (DMC), tetrahydrofuran (THF) and other ethers such as for example 1,4-dioxane, 2-methyltetrahydrofuran (2-MeTHF), methyl t-butyl ether (MTBE), 1,2-dimethoxyethane (DME) and cyclopentyl methylether, mixtures of two or more of these solvents, and mixtures of these solvents with different solvents such as for example methanol (MeOH).

The reaction may be executed at ambient temperature, at an elevated temperature (e.g. reflux), or at low temperature.

As will be clear to a person skilled in the art, the preferred reaction conditions such as solvent and reaction temperature strongly depend on the nature of the specific reaction, in particular on the alkylating or silylation reagent and/or the type of base used in said reaction. When for example benzyl bromide is used as an alkylating reagent, $K_2CO_3$ may be used as a base and the reaction may be executed in a mixture of DCM and MeOH (e.g. a 1:1 mixture) at elevated temperature (reflux). Alternatively, also with benzyl bromide as alkylating reagent, NaOMe may be used as a base and the reaction may be performed in a mixture of 2-methyltetrahydrofuran and methanol at an elevated temperature of around 60° C. When methyl iodide is used as an alkylating reagent, for example $K_2CO_3$ may be used as a base and the reaction may be performed in DMF while keeping the temperature around 20° C.

Extensive purification of the product of step (1a), the obtained 3-protected estrone derivative, is not necessary before the conversion step (1b). In a preferred embodiment, crude 3-protected estrone derivative, i.e. 3-protected estrone derivative that has not undergone extensive purification, is used as starting material for the conversion into 3-protected silyl enol ether III.

As was described above, in a preferred embodiment, step (1a) and (1b) may be executed simultaneously or in a "two-reactions-one-pot" procedure, e.g. by reaction of estrone II with at least two equivalents of a base followed by reaction with at least two equivalents of silylation reagent (such as for example trimethylsilyl chloride or triethylsilyl chloride) in order to introduce A and B, or, alternatively, by reaction of estrone II with at least two equivalents of a base (such as for example LDA), followed by reaction with one equivalent of a silylation agent (such as for example trimethylsilyl chloride) in order to introduce B, followed by reaction with one equivalent of alkylating agent (such as for example benzyl bromide) in order to introduce A.

Step (1b): Conversion of the 17-Keto-Group

Step (1b) relates to the conversion of the keto functionality on $C_{17}$ into the corresponding silyl enol ether to form the 3-protected 17-silyl enol ether 17-B-oxy-3-A-oxy-estra-1,3,5(10),16-tetraene III.

B is a —$Si(R^2)_3$ group, wherein each $R^2$ is independently selected from the group consisting of a $C_1$-$C_6$ alkyl group and a $C_6$-$C_{12}$ aryl group. As was explained above for —$Si(R^1)_3$, each $R^2$ group in —$Si(R^2)_3$ is independently selected, in other words each of the three $R^2$ groups within one —$Si(R^2)_3$ group may be different from the others. Preferably, $R^2$ is selected from the group consisting of methyl, ethyl, propyl, i-propyl, butyl, i-butyl, t-butyl, phenyl, p-tolyl and mesityl. More preferably, B is a trimethylsilyl (TMS) or a triethylsilyl (TES) group. Most preferably, B is a TMS group.

The formation of silyl enol ether III is typically carried out by reacting the 3-protected estrone with a silylation reagent, such as for example a silyl chloride or a silyl triflate, in the presence of a base. Preferably, the silylation reagent is trimethylsilylchloride (TMSCl), trimethylsilyliodide (TMSI) or trimethylsilyltriflate (TMSOTf).

Suitable bases are known to a person skilled in the art, and include for example potassium bases such as $K_2CO_3$ or KH, sodium bases such as NaH or NaOMe, lithium bases such as $LiAlH_4$, LDA, LiTMP or LiHMDS, amine bases such as $Et_3N$, imidazole and 2,6-lutidine, TMEDA, DBU and the like. In a preferred embodiment, the base is LDA or $Et_3N$.

Suitable solvents for the silyl enol ether conversion are known to the person skilled in the art, and include for example dimethylformamide (DMF), dichloromethane (DCM), toluene, tetrahydrofuran (THF) and other ethers such as for example 1,4-dioxane, 2-methyltetrahydrofuran (2-MeTHF), methyl t-butyl ether (MTBE), 1,2-dimethoxyethane (DME) and cyclopentyl methylether, or mixtures thereof.

As will be clear to a person skilled in the art, the preferred reaction conditions such as solvent and reaction temperature strongly depend on the nature of the specific reaction, in particular on the silylation reagent and/or the type of base used in said reaction. For example, when A is benzyl and B is trimethylsilyl (TMS), the reaction may be executed at ambient temperature with TMSOTf as silylation reagent, $Et_3N$ as a base and in toluene or DCM as a solvent.

Extensive purification of silyl enol ether III before subjecting it to the next step of the process is not necessary. In a preferred embodiment, crude III, i.e. III that has not undergone extensive purification, is used as the starting material for step (2).

Step (2): Conversion of 17-B-oxy-3-A-oxy-estra-1, 3,5(10),16-tetraene III into 3-A-oxy-estra-1,3,5(10), 15-tetraen-17-one IV, wherein A is a Protecting Group Step (2) relates to the conversion of silyl enol ether III into α,β-unsaturated enone IV. There are several methods to execute this oxidation.

Method (a): in the Presence of an Iodine(V) Species

In one embodiment of the present invention, step (2) of the process, i.e. the conversion of III into IV, is performed in the presence of an iodine(V) species. Preferably, said iodine(V) species is present in an amount of about 0.001 mol % or more, for example in an amount of about 0.1 mol % or more, or in an amount of about 0.5 mol % or more, with respect to compound III.

In one embodiment, the iodine(V) species is present in an amount of about 100 to about 500 mol % (about 1 to 5 equivalents), preferably in an amount of about 100 to about 300 mol % (about 1 to 3 equivalents), more preferably in an amount of about 100 to about 150 mol % (about 1 to 1.5 equivalents), even more preferably in an amount of about 100 to about 130 mol % (about 1 to 1.3 equivalents), and most preferably in an amount of about 100 mol % (about 1 equivalent), with respect to compound III.

In another, more preferred embodiment, the iodine(V) species is present in an amount of about 100 mol % or less, preferably in an amount of about 75 mol % or less, more preferably in an amount of about 50 mol % or less, even more preferably in an amount of about 30 mol % or less, and even more preferably in an amount of about 20 mol % or less, all with respect to the amount of III. Most preferably, the iodine(V) species is present in an amount of about 15 mol % or less, preferably about 10 mol % or less, more preferably about 5 mol % or less, with respect to the amount of III.

In a preferred embodiment, the iodine(V) species comprises 2-iodoxybenzoic acid (IBX), 2-iodoxybenzenesulphonic acid (IBS), and/or a derivative thereof. The iodine(V) species may be generated in situ. As is known to a person skilled in the art, IBX may for example be generated in situ from 2-iodobenzoic acid and Oxone (2KHSO$_5$.KHSO$_4$.K$_2$SO$_4$), and IBS may for example be generated in situ from 2-iodobenzenesulphonic acid and Oxone.

An example of a derivative of IBX is "stabilised IBX" (SIBX), a formulation comprising IBX, isophthalic acid and benzoic acid disclosed by Ozanne et al., *Org. Lett.* 2003, 5, 2903-2906, incorporated by reference. In a preferred embodiment, the iodine(V) species comprises stabilised IBX.

Other examples of IBX derivatives are, amongst others, 2,3,4,5-tetrafluoro-6-iodoxybenzoic acid (FIBX), disclosed by Richardson et al., *Angew. Chem. Int. Ed.* 2007, 46, 6529-6532, incorporated by reference, and 5-methoxy-3-methyl-2-iodoxybenzoic acid, disclosed by Moorthy et al., *Tetrahedron Lett.* 2008, 49, 80-84, incorporated by reference. An example of an IBS derivative is 5-methyl-2-iodoxybenzenesulphonic acid (5-Me-IBS), disclosed by Yamada, *Spec. Chem. Mag.* 2011, 31, 18-20, incorporated by reference. 5-Me-IBS may for example be generated in situ from 5-methyl-2-iodobenzenesulphonic acid potassium salt and Oxone.

In a preferred embodiment, the iodine(V) species comprises a derivative formed by complexation of IBX, IBS and/or a derivative thereof with a ligand, in particular with dimethyl sulfoxide (DMSO) or with an N-oxide. Examples of suitable N-oxides are N-methylmorpholine-N-oxide (NMO), 4-methoxypyridine-N-oxide (MPO), trimethylamine-N-oxide, 2-picoline-N-oxide and 4-phenylpyridine-N-oxide. Preferably, the ligand is selected from DMSO, NMO, MPO, or a combination of two or more of these ligands.

Said derivatives may be formed for example by stirring a solution of said IBX, IBS and/or derivative thereof with said ligand, optionally at an elevated temperature.

In an alternative embodiment, the iodine(V) species comprises a species formed by activation of I$_2$O$_5$ and/or HIO$_3$ in DMSO. In another alternative embodiment, the iodine(V) species comprises a species formed by complexation of I$_2$O$_5$ and/or HIO$_3$ with a ligand, in particular with an N-oxide as described above.

In another specific embodiment, the iodine(V) species comprises 2-iodoxybenzenesulphonic acid (IBS) and/or a derivative thereof, as described above.

The IBS and/or derivative thereof is then preferably present in an amount of less than 100 mol % (1 equivalent), for example in an amount of about 0.001 to about 50 mol %, preferably about 0.01 to about 40 mol %, more preferably about 0.1 to about 30 mol % even more preferably about 0.5 to about 20 mol % and most preferably about 1 to about 10 mol %, all with respect to compound III.

Suitable solvents for the conversion of III into IV in the presence of an iodine(V) species are known to the person skilled in the art, and include for example dimethyl sulfoxide (DMSO), dimethylformamide (DMF), dimethylacetamide (DMA), N-methylpyrrolidone (NMP), acetonitrile, ethyl acetate, acetone, or a mixture thereof. Alternatively, a mixture of said solvents with other organic solvents such as for example dichloromethane (DCM), chloroform or fluorobenzene may be used. In a preferred embodiment, the solvent is selected from the group consisting of DMSO, DMF, DMA, NMP, a combination thereof, and a combination of DMSO, DMF, DMA and/or NMP with one or more organic solvents, such as for example DCM, chloroform or fluorobenzene. In another preferred embodiment, the reaction is executed in DMSO, or in a mixture of DMSO with one or more organic solvents, such as for example DCM, chloroform or fluorobenzene. In yet another preferred embodiment, the reaction is executed in DMF, or in a mixture of DMF with one or more organic solvents, such as for example DCM, chloroform or fluorobenzene.

The reaction may be executed at ambient temperature or at elevated temperature.

As will be clear to a person skilled in the art, the preferred reaction conditions such as solvent and reaction temperature strongly depend on the nature of the specific reaction, in particular on the type of iodine(V) species that is employed in the reaction.

The conversion of III into IV in the presence of an iodine(V) species, in particular in the presence of IBX, IBS and/or a derivative thereof, proceeds in a very clean way with minimal, if at all, side-product formation. Compound IV is obtained in a good yield and purity.

Method (b): in the Presence of a Transition Metal

In another embodiment of the present invention, step (2) of the process, i.e. the conversion of III into IV, is performed in the presence of a transition metal compound. Preferably, said transition metal compound is present in an amount of about 0.001 mol % or more, for example in an amount of about 0.01 mol % or more, or in an amount of about 0.1 mol % or more, with respect to compound III.

Preferably, the transition metal compound comprises a palladium (Pd) compound, and more preferably, the transition metal is a palladium compound. Examples of palladium compounds are palladium black, Pd(OH)$_2$ on carbon (Pd(OH)$_2$/C, also known as Pearlman's catalyst), Pd(dba)$_2$ or Pd(OAc)$_2$. The palladium compound may also be a ligand-stabilised palladium compound, wherein the palladium is stabilised with for example a bidentate nitrogen or carbene ligand, such as for example palladium stabilised with 1,10-phenanthroline, 2,9-dimethyl-1,10-phenanthroline (neocuproine), 2,2'-bipyridine, etc. The palladium compound may be a palladium(0) or a palladium(II) compound. In a preferred embodiment, the palladium compound comprises a palladium(II) compound, such as for example palladium(II) acetate, Pd(OAc)$_2$. Most preferably, the transition metal compound is palladium(II) acetate.

The transition metal compound may be present in an amount of about 100 mol % (1 equivalent) with respect to compound III, or more. However, it is preferred that the transition metal compound is present in a substoichiometric amount, in other words in an amount of less than about 100 mol % with respect to III. The transition metal compound may for example be present in an amount of 0.01 to about 50 mol %, or in an amount of about 0.1 to about 30 mol %, about 0.5 to about 20 mol %, about 1 to about 15 mol %, or about 3 to about 10 mol %, relative to compound III. Most preferably, the transition metal compound is present in an amount of about 1 to about 5 mol % relative to III.

The reaction may also be performed in the presence of an oxidizing agent (an oxidant) in order to facilitate the reoxidation of the transition metal. The presence of an oxidant is particularly preferred when the transition metal compound is a palladium(0) compound, or when a palladium(II) compound is present in a substoichiometric amount, i.e. in an amount of less than 1 equivalent, with respect to the compound III.

When the reaction is performed in the presence of an oxidant, the oxidant is preferably present in an amount of about 1 equivalent (about 100 mol %) or more, relative to compound III. The amount of oxidant present may range for example from about 1 to about 3 equivalents, preferably from about 1 to about 2 equivalents and more preferably from about 1 to about 1.5 equivalents, relative to the amount of III.

Suitable oxidants are known to a person skilled in the art, and include for example molecular oxygen (O$_2$), copper(II) acetate (Cu(OAc)$_2$), allyl methyl carbonate, t-butylhydroperoxide (TBHP), N-methylmorpholine N-oxide (NMO) and similar N-oxides, benzoquinone, and the like. In a preferred embodiment, the oxidant is copper(II) acetate. In another preferred embodiment, the oxidant is allyl methyl carbonate. In another preferred embodiment, the oxidant is O$_2$.

For example, the reaction may be performed in an O$_2$-atmosphere. It is then preferred that the reaction is executed at atmospheric pressure (about 1 bar). However, execution of the reaction in an O$_2$-atmosphere at elevated pressure is also possible. Alternatively, the reaction may be performed by using the O$_2$ in air as an oxidant. The reaction is then executed in an air atmosphere, either at atmospheric pressure or at an elevated pressure. In addition, the reaction may be performed in "diluted air", such as for example 8% O$_2$ in nitrogen (N$_2$) at elevated pressure, for example at a pressure of about 10 bar or more. In a specific embodiment, the reaction is executed in an O$_2$-atmosphere or an air atmosphere, optionally at an elevated pressure. In another specific embodiment, the reaction is executed in an atmosphere of "diluted air" (e.g. ca. 8% O$_2$ in N$_2$) at an elevated pressure (e.g. about 10 bar or more).

Suitable solvents for the conversion of III into IV in the presence of a transition metal compound, in particular a palladium compound, are known to the person skilled in the art, and include for example dimethyl sulfoxide (DMSO), sulfolane, etc. Additionally, a mixture of said solvents with for example DCM or chloroform may also be used. In a preferred embodiment, the reaction is executed in DMSO, or in a mixture of DMSO with one or more organic solvents, such as for example DCM or chloroform.

The reaction may be executed at ambient temperature or at elevated temperature.

The conversion of III into IV in the presence of transition metal, in particular in the presence of a palladium compound, particularly Pd(OAc)$_2$, proceeds in a very clean way with minimal, if at all, side-product formation. Compound IV is obtained in a good yield and purity.

Step (3): Reduction of the 17-keto group of 3-A-oxy-estra-1,3,5(10),15-tetraen-17-one IV to form 3-A-oxy-estra-1,3,5(10),15-tetraen-17β-ol V, wherein A is a protecting group Step (3) relates to the reduction of the 17-keto functionality to form V, and said reduction of the 17-keto group may be performed as disclosed in WO 2004/041839. Said reduction is preferably performed by reacting 3-A-oxy-estra-1,3,5(10),15-tetraen-17-one IV with a reducing agent selected from the group of metal hydride compounds, said group of metal hydride compounds preferably comprising LiAlH$_4$, AlH$_3$, NaBH$_4$, NaBH(OAc)$_3$, ZnBH$_4$, and NaBH$_4$/CeCl$_3$. Most preferably the metal hydride compound is NaBH$_4$/CeCl$_3$. More preferred reducing agents for use herein are those that will provide a chemo- and stereo-selective reduction of the 17-keto group in favour of the β position. For that reason, the most preferred chemo- and stereo-selective reducing agent for use herein is NaBH$_4$ in combination with CeCl$_3$ hydrate, preferably the heptahydrate.

In particular, it is preferred to suspend 3-A-oxy-estra-1,3,5(10),15-tetraen-17-one IV and CeCl$_3$ heptahydrate in a mixture of a protic solvent, preferably MeOH and THF, and to stir the mixture at room temperature, preferably for about 1 h. A preferred volume ratio of MeOH to THF is 2:1 to 4:1. Then the mixture is cooled, preferably to 0°-5° C., and NaBH$_4$ is added in small portions maintaining the temperature below 8° C. After a period of time, preferably 2 hours, 1 N NaOH and DCM are added. After 30 minutes of stirring, the layers are separated and the aqueous layer is extracted with DCM. The combined organic extracts are dried with sodium sulphate and concentrated to give the product as a white solid.

However, it is even more preferred to quench the reaction mixture with an acid, preferably 2 N HCl, to remove the solvents by distillation under vacuum at about 30° C. to about 40° C. and to add toluene. Preferably, the temperature is then raised to about 70° C. to induce phase separation. The organic phase is then separated, washed with an aqueous solution of Na$_2$CO$_3$ and water. The final organic phase is dried by azeotropic distillation, cooled to about 50° C. and used for the next step.

Step (4): Protection of the 17-OH group of 3-A-oxy-estra-1,3,5(10),15-tetraen-17β-ol V to form 3-A-oxy-17-C-oxy-estra-1,3,5(10),15-tetraene VI, wherein A and C are protecting groups Step (4) of the process relates to the protection of the hydroxyl group on the 17-position of V with a protecting group C, wherein C is a protecting group selected from the group consisting of monofunctional aliphatic hydroxyl protecting groups, i.e. monofunctional protecting groups that are suitable for the protection of an aliphatic hydroxyl group. These protecting groups are known to a person skilled in the art, and described in for example P. J. Kocienski, "*Protecting Groups*", $3^{rd}$ ed., Georg Thieme Verlag, New York 2005, and T. W. Greene et al., "*Protective Groups in Organic Synthesis*", $3^{rd}$ ed., John Wiley & Sons, New York, 1991.

Step (4) may for example be executed as disclosed in WO 2004/041839.

In a preferred embodiment, C is an acetyl protecting group. The 17-OH group is preferably protected by acetylation using a reagent selected from acetic anhydride or acetyl chloride. Preferably, acetic anhydride is used.

In particular, it is preferred to treat a solution of the compound in pyridine with acetic anhydride and 4-dimethylaminopyridine. The mixture is stirred for a period of time. Preferably after 2 hours at room temperature the volatiles are removed. The residue is dissolved in ethyl acetate (EtOAc) and the resulting solution is washed with water and brine. The solution is dried using sodium sulphate and concentrated to give the crude product. Recrystallization from a mixture of organic solvents, preferably ethyl acetate, heptane and ethanol gives the product as a white solid.

Alternatively, the reaction may be performed with a trialkylamine, preferably triethylamine, and an acetyl halide (about two equivalents), preferably acetyl chloride (about 1.5 equivalent) in toluene at about 25° C. to about 60° C., preferably about 40° C. to about 50° C. The work up is then performed by washing with water, aqueous acid and aqueous base. Purification of the product is then achieved by crystallisation, i.e. by removing the toluene by distillation, dissolving the crude product in ethyl acetate and heating this solution to about 70° C. to about 80°. To this heated solution, small portions of ethanol are added to induce crystallisation (preferred ratio of ethyl acetate to ethanol is about 1 to about 8).

Step (5): Oxidation of the carbon-carbon double bond of ring D of 3-A-oxy-17-C-oxy-estra-1,3,5 (10),15-tetraene VI to form protected estetrol VII, wherein A and C are protecting groups Step (5) relates to the oxidation of the carbon-carbon double bond of ring D to form protected estetrol VII, and is preferably executed as is disclosed in WO 2004/041839.

The oxidation of the carbon-carbon double bond in ring D is carried out with an oxidising agent providing selective cis-hydroxylation of the carbon-carbon double bond. Preferably, the oxidising agent is osmium tetroxide ($OsO_4$) and more preferably the oxidising agent is osmium tetroxide immobilized on PVP ($OsO_4$-PVP) that is used in a catalytic amount (cf G. Cainelli et al., *Synthesis* 1989, 45-47) in combination with a co-oxidant selected from trimethylamine-N-oxide, N-methyl morpholine-N-oxide or hydrogen peroxide, preferably trimethylamine-N-oxide. More preferably, $OsO_4$-PVP and trimethylamine-N-oxide are used with THF as the solvent.

In particular, it is preferred to add $OsO_4$-PVP to a heated solution of the compound prepared in the previous step in THF. Preferably, the addition is performed at 50° C. followed by the addition of trimethylamine-N-oxide. Preferably, the addition of trimethylamine-N-oxide is performed portion wise during 1 hour. The mixture is stirred at this temperature for a period of time. Preferably, after 12 hours the mixture is cooled to room temperature and filtered. The volatiles are removed and the residue is dissolved in ethyl acetate and water is added. The aqueous layer is acidified and the layers are separated. The aqueous layer is extracted with ethyl acetate. The combined extracts are dried with sodium sulphate and concentrated. The resulting residue is triturated with heptanes and ethyl acetate to give the product as a white precipitate that is filtered off. The product is purified by recrystallization from a mixture of organic solvents, preferably ethyl acetate, heptane and ethanol to give the product as a white solid.

Step 6: Removal of protecting groups A and C to form estetrol I

Step (6) of the process relates to the removal of the protecting groups A and C to form estetrol I, and is preferably performed as disclosed in WO 2004/041839. WO 2004/041839 discloses that not all protective groups can be removed without adverse effects on the obtained product.

When A is a $C_1$-$C_5$ alkyl group, removal of the protecting group is preferably performed using $BBr_3$. When A is a $C_7$-$C_{12}$ benzylic group, removal of the protecting group is preferably performed using catalytic hydrogenation conditions, for example Pd/$H_2$, as is well known to the person skilled in the art.

In particular, it is preferred to dissolve the protected estetrol VII in a protic solvent, preferably methanol. The conversion is then executed at ambient temperature in the presence of a catalytic amount of Pd/C (e.g. 10%) on carbon (e.g. as a preformed suspension in methanol) in a hydrogen atmosphere, preferably of 1 atmosphere.

Removal of protecting group C is effective using a protic solvent such as methanol and a base, preferably $K_2CO_3$, to yield estetrol.

Alternatively, the order of the two deprotection steps above can be reversed. Thus, the complete deprotection can be accomplished by first removing protecting group C, followed by catalytic hydrogenation to remove protecting group A where A is a protective $C_7$-$C_{12}$ benzylic group. The procedures are identical to the ones described above. However, it is preferred to first remove protecting group A and subsequently protective group C.

Figure 9:
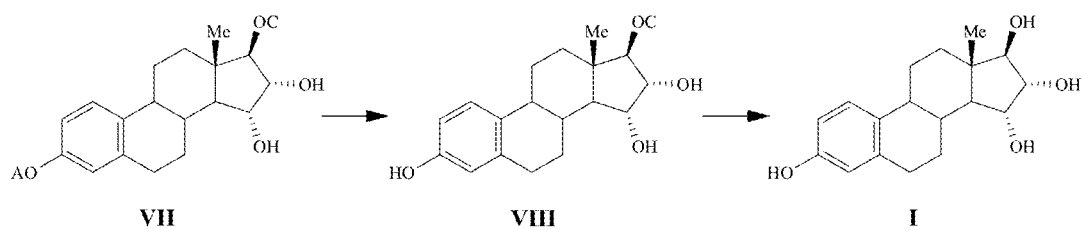
FIG. 9. Scheme 10 depicting the conversion of compound VII to estetrol I.

Therefore, in a preferred embodiment of step (6), protecting group A is removed first to form 17-OC protected estetrol VIII, and subsequently protecting group C is removed to form estetrol I, as is depicted in Scheme 10 shown in FIG. 9.

According to a most preferred embodiment of step (6), the deprotection reactions, i.e. the removal of A and C, are performed in a single step if A is a protective $C_7$-$C_{12}$ benzylic group. Preferably, compound VII is dissolved in a $C_1$-$C_3$ alkyl alcohol, preferably methanol, and subjected to hydrogenation at room temperature. Thereafter, the solution of compound VIII is preferably used in the subsequent step, i.e. the removal of C as described above.

Process for the synthesis of 3-A-oxy-estra-1,3,5(10),15-tetraen-17-one IV

In a second aspect of the invention, the invention relates to a process for the synthesis of 3-A-oxy-estra-1,3,5(10),15-tetraen-17-one IV, wherein A is a protecting group, which comprises the steps of:

(1) conversion of estrone II into 17-B-oxy-3-A-oxy-estra-1,3,5(10),16-tetraene III, wherein A is a protecting group and B is —Si(R$^2$)$_3$; and (2) conversion of 17-B-oxy-3-A-oxy-estra-1,3,5(10),16-tetraene III into 3-A-oxy-estra-1,3,5(10),15-tetraen-17-one IV, wherein A is a protecting group, wherein said conversion of III into IV is performed in the presence of an iodine(V) species, and wherein the iodine(V) species is present in an amount of about 0.1 mol % or more with respect to compound III; wherein A is a protecting group selected from the group consisting of a C$_1$-C$_5$ alkyl group, a C$_7$-C$_{12}$ benzylic group and a —Si(R$^1$)$_3$ group, wherein R$^1$ is independently selected from the group consisting of a C$_1$-C$_6$ alkyl group and a C$_6$-C$_{12}$ aryl group; and B is —Si(R$^2$)$_3$, wherein R$^2$ is independently selected from the group consisting of a C$_1$-C$_6$ alkyl group and a C$_6$-C$_{12}$ aryl group.

Figure 10:
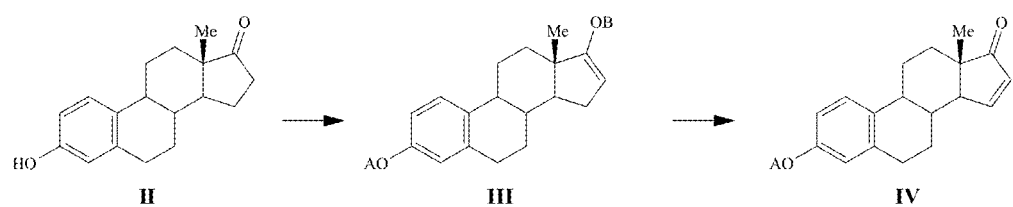
FIG. 10. Scheme 11 depicting synthesis of intermediate 3-A-oxy-estra-1,3,5(10),15-tetraen-17-one IV from estrone II.

Said process is shown in Scheme 11 shown in FIG. 10.

In a preferred embodiment, the iodine(V) species comprises 2-iodoxybenzoic acid (IBX), stabilised 2-iodoxybenzoic acid (SIBX) 2-iodoxybenzenesulphonic acid (IBS), and/or a derivative thereof. A detailed disclosure of this process according to the invention is described above, in step (1) and step (2) of the process for the synthesis of estetrol.

EXAMPLES

General

The following methods and materials for determination were used. $^1$H-NMR spectra were recorded on a Varian 200 MHz apparatus in CD$_3$OD or CDCl$_3$. DSC was measured using a Mettler Toledo DSC822 apparatus.

HPLC-MS was performed using a Hewlett Packard 1100 series (column: Discovery C18 (150×4.6 mm) Supelco; mobile phase: Solution A/Solution B=70/30 (5 min)→(10 min)→10/90 (5 min); flow 1 ml/min; UV: 280 nm; T=22° C.; MS: API-ES negative; Solution A: 9.65 g NH$_4$OAc, 2250 ml H$_2$O, 150 ml MeOH, 100 ml CH$_3$CN; Solution B: 9.65 g NH$_4$OAc, 250 ml H$_2$O, 1350 ml MeOH, 900 ml CH$_3$CN).

Reversed phase HPLC was performed using UV detection at 230 nm, using three different isocratic methods, all at a flow of 1 ml/min and at ambient temperature. Method A used a 250×4.6 mm Supelcosil LC-ABZ column (medium polarity) and methanol/20 mM aqueous phosphate buffer pH 3.8 in a 80/20 ratio. Method B used a 250×4 mm Nucleosil C-18 column and H$_2$O/MeOH/acetonitrile in a 15/50/35 ratio, containing 50 mM ammonium acetate. Method C used a 250×4 mm Nucleosil C-18 column and methanol/20 mM aqueous phosphate buffer pH 3.8 in a 80/20 ratio.

Example 1

3-Benzyloxy-estra-1,3,5(10)-trien-17-one (3-protected estrone, A is benzyl)

To a suspension of estrone (II; 100 g, 0.370 mol) and K$_2$CO$_3$ (160 g, 1.16 mol) in DCM/MeOH (800 ml, 1:1 v/v ratio) at room temperature (RT) was added benzyl bromide (132 ml, 1.10 mol) in one portion. The resulting mixture was refluxed for 16 h (50% conversion after 4 h according to TLC). The reaction mixture was cooled to RT and solids were filtered off. The filter-cake was washed with MeOH. The solution was concentrated (to a total volume of ca. 300 ml). The precipitate that had formed was collected by filtration and washed with heptanes to give a white solid. The filtrate was concentrated further (to a total volume of 100 ml) and triturated with heptane. The resulting precipitate was filtered off and combined with the first batch of product. The product (153 g, max 0.370 mol) still contained traces off benzyl bromide but was used without further purification. The product can be purified by recrystallization from DCM/MeOH (1/2).

TLC: R$_f$=0.5 (heptanes/ethyl acetate=4/1); HPLC-MS: 91%; $^1$H-NMR (200 MHz, CDCl$_3$) δ 7.60-7.24 (m, 5H), 7.49 (d, 1H, J=8.4 Hz), 6.87 (dd, 1H, J$_1$=2.6 Hz, J$_2$=8.4 Hz), 6.82 (d, 1H, J=2.4 Hz), 5.12 (s, 2H), 3.05-2.90 (m, 2H), 2.66-2.01 (m, 5H), 1.77-1.47 (m, 8H), 0.99 (s, 3H) ppm.

Example 2

3-Benzyloxy-17-trimethylsilyloxy-estra-1,3,5(10),16-tetraene (compound III, A is benzyl, B is trimethylsilyl)

3-Benzyloxy-estra-1,3,5(10)-trien-17-one (3-protected estrone, A is benzyl; 238 mg, 0.660 mmol) was dissolved in DCM (10 ml). Et$_3$N (0.166 ml, 1.188 mmol) and TMS-OTf (0.143 ml, 0.792 mmol) were added and the solution was stirred at ambient temperature for 1 h. According to TLC (alumina, heptane/ethyl acetate 4/1 plus Et$_3$N). The entire content of the flask was transferred onto a small column of basic alumina (type II) and eluted with heptane/ethyl acetate 4/1 plus Et$_3$N. The product was obtained as a white solid (248 mg, 87%).

Example 3

3-Benzyloxy-estra-1,3,5(10),15-tetraen-17-one (compound IV, A is benzyl)

Unstabilised IBX (1.0 g; 3.6 mmol), a catalytic amount of trimethylamine-N-oxide (40 mg, 10 mol %) and 3 Å molecular sieves (100 mg) were added to 10 ml dry DMSO.

A fluorobenzene solution containing about 2.8 mmol crude (94% GC) benzylestrone-trimethylsilyl enol ether III (4.5 ml; corresponding to 1.0 g ketone) was added, giving a sudden solidification of the reaction mixture due to precipitated substrate. Mild heating to 40-45° C. was needed for dissolution. After 1 h HPLC showed a clean conversion of the enol ether to the enone with some ketone present due to advantageous hydrolysis.

Example 4

3-Benzyloxy-estra-1,3,5(10),15-tetraen-17-one (compound IV, A is benzyl)

Stabilised 2-iodoxybenzoic acid (SIBX, 0.5 g; 0.8 mmol oxidant) was dissolved in 4 ml anhydrous DMSO containing 0.8 mmol of amine-N-oxide cocatalyst. These mixtures were pre-incubated for 30 minutes at ambient temperature. To this solution was added a solution of benzylestrone-trimethylsilyl enol ether III (0.215 g; 0.5 mmol) in 1 ml anhydrous fluorobenzene. The solidified mixtures were heated slightly to 30-35° C. to enable mixing. After 20-30 minutes the reaction mixtures became homogeneous. HPLC analysis by showed a clean conversion of the enol ether to the enone, with in some cases some ketone present due to hydrolysis. Results are summarized in Table 1.

TABLE 1

SIBX mediated dehydrogenation of TMS enol ether, in the presence of co-catalyst.

| Entry | Co-catalyst | Time (h) | Conversion (%) | Enone selectivity (%) |
|---|---|---|---|---|
| 1 | 4-Methoxypyridine-N-oxide | 1 | 94 | 75 |
| 2 | 4-Methoxypyridine-N-oxide | 3 | >99[1] | 80 |
| 3 | Trimethylamine-N oxide[2] | 1 | 100 | 68 |
| 4 | Trimethylamine-N oxide[3] | 1 | 100 | 63 |
| 5 | 4-Methoxypyridine-N-oxide[4] | 1 | >99 | 72 |

[1] 19% ketone present due to hydrolysis.
[2] Anhydrous 4-methoxypyridine-N-oxide.
[3] 4-Methoxypyridine-N-oxide dihydrate.
[4] Anhydrous 4-Methoxypyridine-N-oxide.

Example 5

3-Benzyloxy-estra-1,3,5(10),15-tetraen-17-one (compound IV, A is benzyl)

Stabilised 2-iodoxybenzoic acid (SIBX, 0.5 g; 0.8 mmol oxidant) was dissolved in 4 ml anhydrous dimethylformamide (DMF) containing 0.8 mmol of N-methylmorpholine-N-oxide cocatalyst. These mixtures were pre-incubated for 30 minutes at ambient temperature. To this solution was added solid benzylestrone-trimethylsilyl enol ether III (0.215 g; 0.5 mmol). The reaction mixture was agitated for 1 hour at ambient temperature and then further heated to 40° C. The total reaction time was 2 hours. Results are summarized in Table 2.

TABLE 2

SIBX mediated dehydrogenation of TMS enol ether in DMF.

| Entry | Solvent | Time (h) | Conversion (%) | Enone selectivity (%) |
|---|---|---|---|---|
| 1 | dimethylformamide (DMF) | 0.5 | 83 | 86 |
| 2 | dimethylformamide (DMF) | 1 | 99 | 86 |
| 3 | dimethylformamide (DMF) | 2 | >99[1] | 85 |

[1] 14% hydrolysis.

Example 6

3-Benzyloxy-estra-1,3,5(10),15-tetraen-17-one (compound IV, A is benzyl)

An 8 ml vial equipped with a stirring bar was charged under air with compound III (A is benzyl, B is trimethylsilyl; 50 mg, 0.116 mmol), palladium acetate (2.6 mg, 0.116 mmol) and DMSO (dry, 0.9 ml), chloroform (0.1 ml). The vial was purged with pure oxygen gas and kept under an oxygen atmosphere with a balloon. The mixture was stirred at 35° C. overnight. Complete conversion was obtained according to TLC (Si, n-heptane/ethyl acetate 4/1). Clean conversion into the desired product was obtained according to HPLC.

An 8 ml vial equipped with a stirring bar was charged under air with compound III (A is benzyl, B is trimethylsilyl; 100 mg, 0.231 mmol), palladium acetate (5.19 mg, 0.023 mmol) and DMSO (dry, 0.9 ml), DCM (0.1 ml). The vial was purged with pure oxygen gas and kept under an oxygen atmosphere with a balloon. The mixture was stirred at 35° C. overnight. Complete conversion was obtained according to TLC (Si, n-heptane/ethyl acetate 4/1). Clean conversion into the desired product IV was obtained according to HPLC.

Example 7

3-Benzyloxy-estra-1,3,5(10),15-tetraen-17-one (compound IV, A is benzyl)

Benzylestrone-trimethylsilyl enol ether III (0.20/0.215 g; 0.5 mmol) and allyl methyl carbonate (0.115 ml; 1.0 mmol) were mixed with 4.5 ml anhydrous acetonitrile. Palladium acetate stock solution (0.25 ml; 5 μmol; 1 mol %) in acetonitrile was added and the mixture was stirred in an argon atmosphere at 75° C. HPLC analysis after 67 hours showed a complete conversion of the enol ether with a 51% selectivity for the enone IV.

Example 8

3-Benzyloxy-estra-1,3,5(10),15-tetraen-17-ol (compound V A is benzyl)

To a solution of 3-benzyl-dehydroestrone (compound IV; A=benzyl; 58 g, 162 mmol) in a mixture of MeOH (900 ml) and THF (200 ml) at room temperature was added $CeCl_3$ heptahydrate (66.4 g, 178 mmol). After stirring for 1 h the mixture was cooled to 0-5° C. using an ice/water bath. Then $NaBH_4$ (12.2 g, 324 mmol) was added in small portions maintaining a temperature below 8° C. After stirring for 2 h at 0-5° C. (TLC showed the reaction to be complete) 1 N NaOH (300 ml) and DCM (1 l) were added and the mixture was stirred for ½ h at room temperature. The layers were separated and the aqueous layer was extracted with DCM (200 ml). The organic layers were combined, dried ($Na_2SO_4$) and concentrated in vacuo to give an off-white solid (55.0 g, 152.8 mmol, 94%).

TLC: $R_f$=0.25 (heptanes/ethyl acetate=4:1); HPLC-MS: 93% β-isomer, 2% α-isomer; DSC: Mp. 149.7° C., purity 96.6%; $^1$H-NMR (200 MHz, $CDCl_3$) δ 7.48 (m, 5H), 7.27 (d, 1H, J=8.4 Hz), 6.85 (dd, 1H, $J_1$=2.8 Hz, $J_2$=8.6 Hz), 6.81 (d, 1H, J=2.4 Hz), 6.10 (d, 1H, J=5.8 Hz), 5.79 (dd, 1H, $J_1$=1.8 Hz, $J_2$=3.4 Hz), 5.11 (s, 2H), 4.48 (d, 1H, J=7.6), 2.96 (m, 2H), 2.46-1.64 (m, 9H), 0.93 (s, 3H) ppm.

Example 9

17-Acetyloxy-3-benzyloxy-estra-1,3,5(10),15-tetraene (compound VI, A is benzyl, C is acetyl)

A solution of 3-benzyloxy-estra-1,3,5(10),15-tetraen-17-ol (compound V; A=benzyl; 55.0 g, max. 153 mmol) in pyridine (400 ml) was treated with $Ac_2O$ (50 ml, 0.53 mol) and 4-dimethylaminopyridine (1.5 g, 12.3 mmol). The mixture was stirred for 2 h at room temperature (TLC showed the reaction to be complete). It was concentrated in vacuo. The residue was dissolved in EtOAc (400 ml), washed with water (200 ml) and brine (150 ml), dried ($Na_2SO_4$) and concentrated in vacuo to yield a yellow solid (54.0 g, 49.8 mmol, 88%). The product was purified by recrystallization from heptanes/EtOAc/EtOH (1:0.5:1) to afford a white solid (45.0 g, 112 mmol, 73%).

TLC: $R_f$=0.6 (heptanes/ethyl acetate=4/1); HPLC-MS: 98% β-isomer, 1% α-isomer, 1.3% B-estradiol; DSC: Mp. 122.8° C., purity 99.8%; $^1$H-NMR (200 MHz, CDCl$_3$) δ 7.44 (m, 5H), 7.27 (d, 1H, J=8.4 Hz), 6.86 (dd, 1H, $J_1$=2.6 Hz, $J_2$=8.4 Hz), 6.80 (d, 1H, J=2.6 Hz), 6.17 (d, 1H, J=5.8 Hz), 5.78 (dd, 1H, $J_1$=1.4 Hz, $J_2$=3.2 Hz), 5.45 (m, 1H), 5.11 (s, 2H), 2.96 (m, 2H), 2.40-1.54 (m, 10H), 2.18 (s, 3H), 0.93 (s, 3H) ppm.

Example 10

17-Acetyl-3-benzyl estetrol (compound VII, A is benzyl, C is acetyl)

OsO$_4$ on PVP (9 g, ~5% w/w OsO$_4$ on PVP, prepared according to Cainelli et al. *Synthesis* 1989, 45-47 was added to a solution of 17-acetyloxy-3-benzyloxy-estra-1,3,5(10),15-tetraene (compound VI; A=benzyl, C=acetyl; 45 g, 112 mmol) in THF (450 mL) and the mixture was heated to 50° C. Trimethylamine-N-oxide dihydrate (24.9 g, 224 mmol) was added portion-wise over 2 h. After stirring for 36 h at 50° C. (TLC showed the reaction to be complete) the reaction mixture was cooled to room temperature. The solids were filtered off, washed with THF (100 ml) and the filtrate was concentrated. The residue was taken up in EtOAc (250 ml) and water (250 ml) was added. The aqueous layer was acidified with 1 N HCl (ca. 10 ml). The layers were separated and the aqueous layer was extracted with EtOAc (150 ml). The organic layers were combined, dried (Na$_2$SO$_4$) and concentrated in vacuo. The residue was triturated with heptanes/EtOAc (1:1, 100 ml), stirred for 2 h and the resulting white precipitate was filtered off to give the product as a white solid (41 g, 94 mmol, 84%). The product was purified by recrystallization from heptanes/ethyl acetate/EtOH (2:1:1) three times to afford a white solid (21 g, 48.2 mmol, 43%).

HPLC-MS: 99.5% βαα-isomer; DSC: Mp. 159.3° C., purity 98.7%; $^1$H-NMR (200 MHz, CDCl$_3$) δ 7.49 (m, 5H), 7.27 (d, 1H, J=8.4 Hz), 6.84 (dd, 1H, $J_1$=2.6 Hz, $J_2$=8.4 Hz), 6.81 (d, 1H, J=2.4 Hz), 5.11 (s, 2H), 4.45 (d, 1H, J=4.4), 4.11 (m, 3H), 3.12 (m, 1H) 2.95 (m, 2H), 2.46-1.64 (m, 10H), 2.24 (s, 3H), 0.93 (s, 3H) ppm.

Example 11

17 Acetyl estetrol (compound VIII; C is acetyl)

To a solution of 17-acetyl-3-benzyl estetrol (compound VII; A=benzyl, C=acetyl; 21 g, 48.2 mmol) in MeOH (600 ml, HPLC-grade) was added a preformed suspension of 10% Palladium on activated carbon (2 g) in methanol (50 ml). The mixture was placed under an atmosphere of H$_2$ at 1 atm and stirred for 24 h (TLC showed the reaction to be completed) at room temperature. It was filtered over Celite® and the filter cake was washed with MeOH (200 ml). The filtrate was concentrated in vacuo to give 17-acetyl estetrol as a white solid (15 g, 43.4 mmol, 90%).

TLC: $R_f$=0.2 (heptanes/ethyl acetate=1/1); HPLC-MS: 99.2%, DSC: Mp. 212.2° C., purity 98.9%; $^1$H-NMR (200 MHz, CD$_3$OD) δ 7.14 (d, 1H, J=8.0 Hz), 6.60 (dd, 1H, $J_1$=2.6 Hz, $J_2$=8.8 Hz), 6.56 (d, 1H, J=2.4 Hz), 4.81 (dd, 1H, $J_1$=3.4 Hz, $J_2$=6.4 Hz), 4.07 (m, 3H), 3.12 (m, 1H), 2.85 (m, 2H), 2.37-1.37 (m, 10H), 2.18 (s, 3H), 0.91 (s, 3H) ppm.

Example 12

Estetrol

17-Acetyl-estetrol (compound VIII; C=acetyl; 15 g, 43.4 mmol) and K$_2$CO$_3$ (6 g, 43.4 mmol) were suspended in MeOH (500 ml, HPLC-grade) and stirred for 4 h at room temperature (TLC showed the reaction to be complete). The solvents were evaporated in vacuo. Water (200 ml) and CHCl$_3$ (70 ml) were added and the mixture was stirred and neutralized with 0.1 N HCl (50 ml). The product was collected by filtration, washed with water (100 ml) and CHCl$_3$ (100 ml) to give estetrol as a white solid (12.2 g, 40.1 mmol, 92.5%) after drying at 40° C. in an air-ventilated oven. TLC: $R_f$=0.05 (heptanes/ethyl acetate=1/1); HPLC-MS: 99.1%, DSC: Mp. 243.7° C., purity 99.5%; $^1$H-NMR (200 MHz, CD$_3$OD) δ 7.14 (d, 1H, J=8.6 Hz), 6.61 (dd, 1H, $J_1$=2.6 Hz, $J_2$=8.4 Hz), 6.56 (d, 1H, J=2.4 Hz), 4.83 (m, 1H), 3.93 (m, 3H), 3.50 (d, 1H, J=5.2), 3.38 (m, 2H), 2.84 (m, 2H), 2.32 (m, 3H), 1.97 (m, 1H), 1.68-1.24 (m, 5H), 0.86 (s, 3H) ppm.

The invention claimed is:
1. A process for the preparation of estra-1,3,5(10)-trien-3,15α,16α,16α,17β-tetraol I, which comprises the steps of:

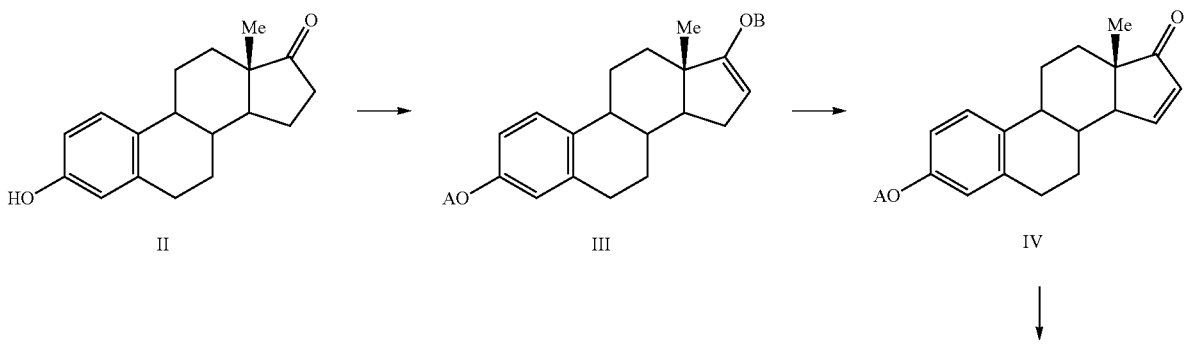

-continued

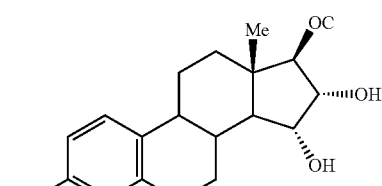

VII

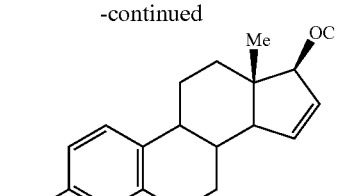

VI

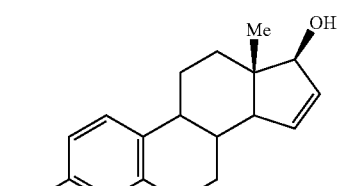

V

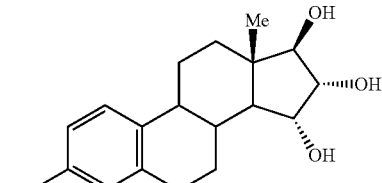

I (1) conversion of estrone II into 17-B-oxy-3-A-oxy-estra-1,3,5(10),16-tetraene III, wherein A is a protecting group and B is —Si(R²)₃;
(2) conversion of 17-B-oxy-3-A-oxy-estra-1,3,5(10),16-tetraene III into 3-A-oxy-estra-1,3,5(10),15-tetraen-17-one IV, wherein A is a protecting group;
(3) reduction of the 17-keto group of 3-A-oxy-estra-1,3,5(10),15-tetraen-17-one IV to form 3-A-oxy-estra-1,3,5(10),15-tetraen-17β-ol V, wherein A is a protecting group;
(4) protection of the 17-OH group of 3-A-oxy-estra-1,3,5(10),15-tetraen-17β-ol V to form 3-A-oxy-17-C-oxy-estra-1,3,5(10),15-tetraene VI, wherein A and C are protecting groups;
(5) oxidation of the carbon-carbon double bond of ring D of 3-A-oxy-17-C-oxy-estra-1,3,5(10),15-tetraene VI to form protected estetrol VII, wherein A and C are protecting groups; and
(6) removal of protecting groups A and C to form estetrol I;
wherein:
A is a protecting group selected from the group consisting of a C7-C12 benzylic group and a —Si(R¹)3 group, wherein R¹ is independently selected from the group consisting of a C₁-C₆ alkyl group and a C₆-C₁₂ aryl group;
B is —Si(R²)3, wherein R² is independently selected from the group consisting of a C₁-C₆ alkyl group and a C₆-C₁₂ aryl group; and
C is a protecting group selected from the group consisting of monofunctional aliphatic hydroxyl group protecting groups;
and wherein step (2) of the process is performed in the presence of an iodine (V) species, wherein the iodine (V) species is present in an amount of 0.1 mol % or more with respect to compound III, and wherein the iodine(V) species comprises 2-iodoxybenzoic acid (IBX), stabilised 2-iodoxybenzoic acid (SIBX), 2-iodoxybenzenesulphonic acid (IBS), and/or a derivative thereof selected from the group consisting of 2,3,4,5-tetrafluoro-6-iodoxybenzoic acid (FIBX), 5-methoxy-3-methyl-2-iodoxybenzoic acid, and 5-methyl-2-iodoxybenezensulphonic acid (5-Me-IBS).

2. The process according to claim 1, wherein the iodine (V) species comprises a species formed by complexation of IBX, IBS and/or a derivative thereof selected from the group consisting of stabilized 2-iodoxybenzoic acid (SIBX), 2,3,4,5-tetrafluoro-6-iodoxybenzoic acid (FIBX), 5-methoxy-3-methyl-2-iodoxybenzoic acid, and 5-methyl-2-iodoxybenzenesulphonic acid (5-Me-IBS) with a ligand.

3. The process according to claim 1, wherein the iodine (V) species comprises 2-iodoxybenzenesulphonic acid (IBS) and/or a 5-methyl-2-iodoxybenzenesulphonic acid (5-Me-IBS), and wherein the IBS and/or 5-methyl-2-iodoxybenzenesulphonic acid (5-Me-IBS) is present in an amount of 0.1 mol % to 50 mol % with respect to compound III.

4. The process according to claim 1, wherein the solvent in step (2) is selected from the group consisting of DMSO, DMF, DMA, NMP, a combination thereof, and a combination of DMSO, DMF, DMA and/or NMP with one or more organic solvents.

5. The process according to claim 1, wherein step (2) of the process is performed in the presence of a transition metal compound, and wherein the transition metal compound is present in an amount of 0.1 mol % to 30 mol % with respect to compound III.

6. The process according to claim 1, wherein step (2) of the process is performed in the presence of a transition metal compound, and wherein the transition metal compound is present in an amount of 0.1 mol % to 50 mol % with respect to compound III, and wherein an oxidant is further present.

7. The process according to claim 1, wherein the oxidant is molecular oxygen (O₂), allyl methyl carbonate and/or copper(II) acetate.

8. The process according to claim 1, wherein the solvent in step (2) is selected from the group consisting of DMSO, or a combination of DMSO with one or more organic solvents.

9. The process according to claim 1, wherein B is a trimethylsilyl or a triethylsilyl group.

10. The process for the synthesis of 3-A-oxy-estra-1,3,5(10),15-tetraen-17-one IV, wherein A is a protecting group, which comprises the steps of:

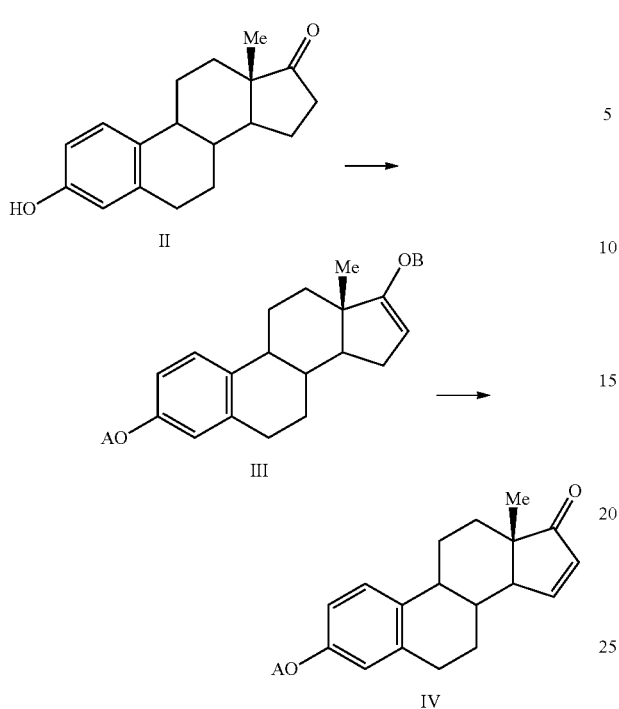

(1) conversion of estrone II into 17-B-oxy-3-A-oxy-estra-1,3,5(10),16-tetraene III, wherein A is a protecting group and B is —Si(R²)₃; and (2) conversion of 17-B-oxy-3-A-oxy-estra-1,3,5(10),16-tetraene III into 3-A-oxy-estra-1,3,5(10),15-tetraen-17-one IV, wherein A is a protecting group, wherein said conversion of III into IV is performed in the presence of an iodine(V) species, and wherein the iodine(V) species is present in an amount of 0.1 mol % or more with respect to compound III;

wherein:

A is a protecting group selected from the group consisting of a $C_7$-$C_{12}$ benzylic group and a —Si(R¹)₃ group, wherein R¹ is independently selected from the group consisting of a $C_1$-$C_6$ alkyl group and a $C_6$-$C_{12}$ aryl group; and B is —Si(R²)₃, wherein R² is independently selected from the group consisting of a $C_1$-$C_6$ alkyl group and a $C_6$-$C_{12}$ aryl group, and wherein the iodine(V) species comprises 2-iodoxybenzoic acid (IBX), 2-iodoxybenzenesulphonic acid (IBS), stabilised 2-iodoxybenzoic acid (SIBX), and/or a derivative thereof selected from the group consisting of 2,3,4,5-tetrafluoro-6-iodoxybenzoic acid (FIBX), 5-methoxy-3-methyl-2-iodoxybenzoic acid, and 5-methyl-2-iodoxybenzenesulphonic acid (5-Me-IBS).

11. The process according to claim 2, wherein the ligand is DMSO or an N-oxide.

12. The process according to claim 6, wherein the oxidant is present in an amount of from about 1 to about 3 equivalents, relative to the amount of III.

* * * * *

UNITED STATES PATENT AND TRADEMARK OFFICE
CERTIFICATE OF CORRECTION

| | | |
|---|---|---|
| PATENT NO. | : 10,844,088 B2 | Page 1 of 1 |
| APPLICATION NO. | : 15/426209 | |
| DATED | : November 24, 2020 | |
| INVENTOR(S) | : Johannes Jan Platteeuw et al. | |

It is certified that error appears in the above-identified patent and that said Letters Patent is hereby corrected as shown below:

On the Title Page

Item (73), please correct the name of the Assignee to read:
-- MITHRA R&D SA --

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*